United States Patent [19]
Bridges

[11] Patent Number: 5,829,437
[45] Date of Patent: Nov. 3, 1998

[54] MICROWAVE METHOD AND SYSTEM TO DETECT AND LOCATE CANCERS IN HETEROGENOUS TISSUES

[75] Inventor: Jack E. Bridges, Park Ridge, Ill.

[73] Assignee: Interstitial, Inc., Park Ridge, Ill.

[21] Appl. No.: 641,834

[22] Filed: May 2, 1996

Related U.S. Application Data

[63] Continuation-in-part of Ser. No. 492,998, Jun. 21, 1995, which is a continuation-in-part of Ser. No. 269,691, Jul. 1, 1994, abandoned.

[51] Int. Cl.[6] .................................................. A61B 5/05
[52] U.S. Cl. ...................................... 128/653.1; 324/638
[58] Field of Search ........................ 128/653.1; 324/637, 324/638, 639; 607/89, 101; 600/10, 12; 606/27, 33–45

[56] References Cited

U.S. PATENT DOCUMENTS

| | | | |
|---|---|---|---|
| 4,135,131 | 1/1979 | Larsen et al. | 128/653.1 |
| 4,641,659 | 2/1987 | Sepponen | 128/653.1 |
| 4,765,179 | 8/1988 | Fuller et al. | 73/53 |
| 4,774,961 | 10/1988 | Carr | 128/653.1 |
| 4,805,627 | 2/1989 | Klingenbeck | 128/653.1 |
| 5,363,050 | 11/1994 | Guo et al. | 128/653.1 |
| 5,481,196 | 1/1996 | Nosov | 128/653.1 |
| 5,662,110 | 9/1997 | Carr | 128/653.1 |

*Primary Examiner*—Brian L. Casler
*Attorney, Agent, or Firm*—Dorn, McEachran, Jambor & Keating

[57] ABSTRACT

A method and system for detecting an incipient tumor in living tissue such as that of a human breast in accordance with differences in relative dielectric characteristics. A generator produces a non-ionizing electromagnetic input wave of preselected frequency, usually exceeding three gigahertz, and that input wave is used to irradiate the living tissue, being effectively focused into a minute, discrete volume within the tissue to develop a non-ionizing electromagnetic wave at that position. The illumination location is shifted over a portion of the living tissue in a predetermined scanning pattern. Backscatter signal returns from the living tissue are collected to develop a backscatter return signal wave. The backscatter wave is processed to segregate skin tissue backscatter to develop a segregated backscatter wave signal; that segregated signal, in turn, is employed to detect any anomaly, caused by differences in relative dielectric characteristics, that is indicative of the presence of a tumor or other abnormality in the scanned living tissue.

51 Claims, 16 Drawing Sheets

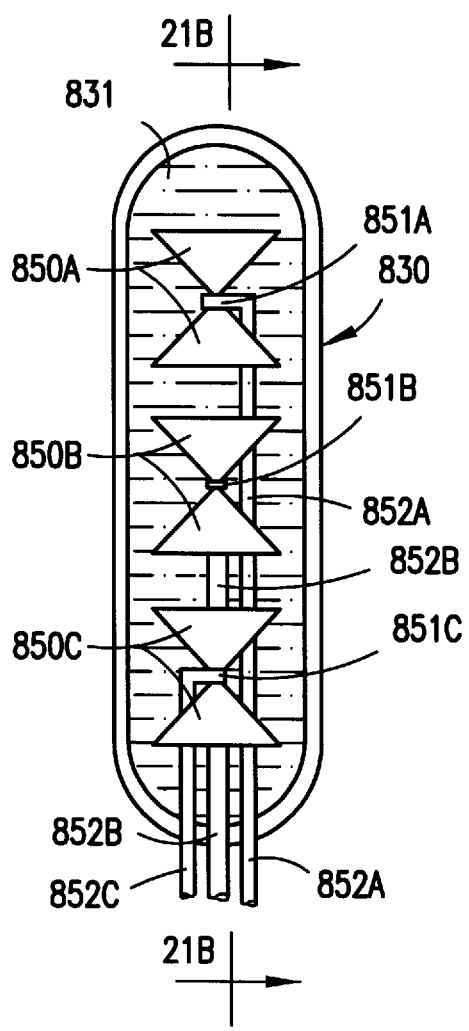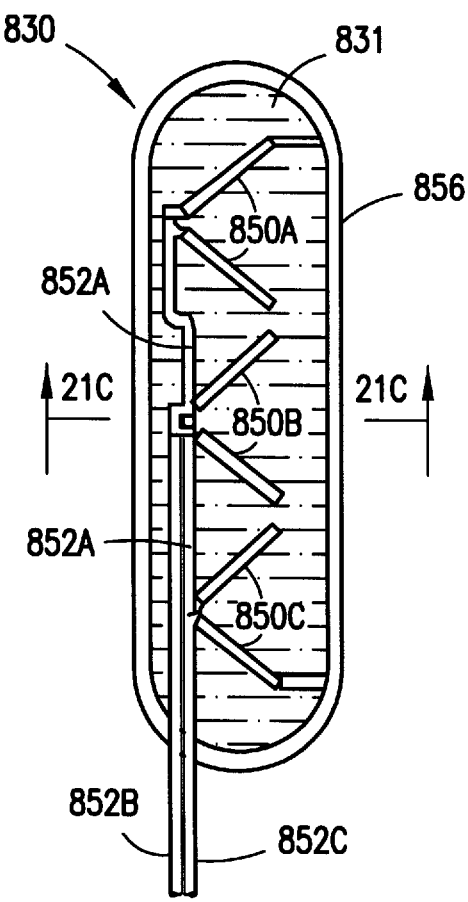
FIG. 21A
FIG. 21B
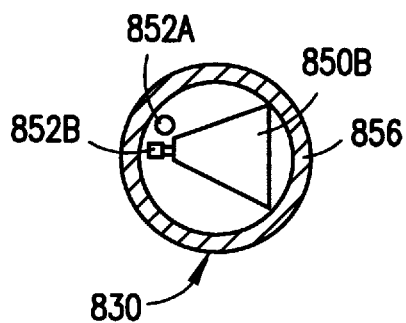
FIG. 21C

MICROWAVE METHOD AND SYSTEM TO DETECT AND LOCATE CANCERS IN HETEROGENOUS TISSUES

This application is a continuation-in-part of application Ser. No. 08/492,998 filed Jun. 21, 1995, which was a continuation-in-part of application Ser. No. 08/269,691 filed Jul. 1, 1994, now abandoned.

BACKGROUND OF THE INVENTION

Breast cancer is one of the leading causes of death for women. About one out of eight or nine women are expected to develop tumors of the breast, and about one out of sixteen to twenty are expected to die prematurely from breast cancer.

Mammography or other X-ray methods are currently most used for detection of breast cancers. However, every time a mammogram is taken, the patient incurs a small risk of having a breast tumor induced by the ionizing radiation properties of the X-rays used during the mammogram. Also, the process is costly and sometimes imprecise. Accordingly, the National Cancer Institute has not recommended mammograms for women under fifty years of age, who are not as likely to develop breast cancers as are older women. However, while only about twenty two percent of breast cancers occur in women under fifty, data suggests that breast cancer is more aggressive in pre-menopausal women. Furthermore, women under forty are getting the disease in increasing numbers—about eleven thousand annually now—and no one knows why.

Mammograms require interpretation by radiologists. One radiologist has said "I generally can spot cancers between five and ten millimeters in diameter. The prognosis is excellent then." However, about ten to fifteen percent of tumors of this size are not detected. One study showed major clinical disagreements for about one-third of the same mammograms that were interpreted by a group of radiologists. Further, many women find that undergoing a mammogram is a decidedly painful experience.

Thus, alternative methods to detect breast cancers are needed, especially non-invasive methods that do not entail added risks, that can detect tumors as small as two millimeters in diameter, that are not unduly unpleasant to the patient, and that can be used for early detection. Such a screening system is needed because extensive studies have demonstrated that early detection of small breast tumors leads to the most effective treatment. While X-ray mammography can detect lesions of approximately five mm or larger, the accuracy may range between 30% and 75%, depending on the skill of the diagnostic radiologist. Repeated X-ray examinations, however, are not encouraged because these may become carcinogenic. These considerations, in addition to cost considerations, have led physicians to recommend that women wait until the age of fifty before having routine mammograms.

One solution would be a non-ionizing, non-invasive, and low cost detection or screening method to detect very small malignant breast tumors. It could greatly increase without hazard the number of patients examined and would identify those patients who need diagnostic X-ray examinations, where the added hazards and costs could be justified.

About one in eight women develop breast cancers and about one in sixteen die prematurely from this disease. Despite strong encouragement, less than half of the millions of women who should be are routinely screened. Some of the reasons are cost and discomfort experienced during mammography. Other concerns are the additional risks associated with ionizing radiation, especially for routine exams for women under fifty. However, while only twenty two percent of breast cancers occur in women under fifty, data suggest that breast cancer is more aggressive in pre-menopausal women. A screening procedure need only identify breasts with abnormalities. The precision and imaging requirements associated with diagnostic purposes and treatment monitoring, while desirable, need not apply.

Further, mammography fails to detect between five and twenty-five percent of malignant breast cancers. While many tumors are detected by mammography, the method is not capable of determining whether the tumor is benign or malignant. When a tumor is detected, a biopsy must be made to determine the nature of the tumor. Less than twenty percent of the tumors detected in mammograms are found to be malignant, but the biopsy is both painful and costly. Thus, a complementary method is needed that uses a different modality, such as microwaves, that may be beneficial in reducing the number of false negatives and false positives.

In the case of prostate cancers detected by the prostate-specific antigen test (PSA), a large proportion are not aggressive and can be treated by conservative methods. However, the PSA cannot always distinguish those that are more aggressive. In some cases, transrectal ultrasound is used as a method to assess the size and growth rate. The ultrasound results, in combination with tracking of the increase in PSA levels, may help to determine whether or not more aggressive treatment methods are needed. Even with this combined method, statistical methods have been proposed to better estimate the volume of the cancer and the need for aggressive treatment. Thus, there is a need for a different and new modality that would complement ultrasound.

There are several generic cancer detection methods: sonic, chemical, nuclear and non-ionizing electromagnetic. The sonic, chemical and nuclear (such as MRI) techniques have been under study for some time and, while some interesting approaches are being followed, none have been publicized as being available in the near future for low cost screening.

The method proposed here is not like the non-ionizing electromagnetic methods that have been studied. Studies have considered the use of electromagnetic, non-ionizing methods to detect or image portions of the human body. An excellent summary of such activity is presented in a publication entitled "Medical Applications of Microwave Imaging", edited by L. E. Larsen and J. H. Jacobi, IEEE Press 1986.* These activities include microwave thermography, radar techniques to image biological tissues, microwave holography and tomography, video pulse radar, frequency modulation pulse compression techniques for biological imaging, microwave imaging with diffraction tomography, inverse scattering approaches, and medical imaging using an electrical impedance. The publications in this book contain about five hundred citations, some of which are duplicates. The technology cited not only includes electromagnetic disciplines, but also notes related studies in sonic imaging and seismic imaging. To update these data, the IEEE transactions on Medical Imaging, Biomedical Engineering, Microwave Theory and Techniques and Antennas and Propagation have been reviewed. Also surveyed was the publication Microwave Power and Engineering. This update has indicated little significant progress in the aforementioned electromagnetic techniques that would be important to detect breast and prostate cancers. Breast and prostate cancer detection systems based on the concepts described in this specification were not presented.

* See the list of references at the end of this specification.

Many important reasons exist for this lack of progress. In the case of microwave thermography, adequate depth of penetration, along with the required resolution, may not be realized, except for large cancers. In the case of holography, reflections at the skin-air interface tend to mask the desired returns from breast tumors beneath the skin. Further, illuminating the entire volume of a breast either requires excessive power (with possible biological hazards) or acceptance of poor signal-to-noise ratios. In the case of through-the-body electromagnetic techniques, such as tomography, the attenuation characteristics of the body are such that long wavelengths are usually used, with an attendant loss of resolution. Imaging by determining perturbations in body impedance caused by the presence of tumors as sensed by multi-electrode arrays have been either inadequate in sensitivity or subject to false alarms. A major difficulty with some of the multi-electrode or multi-antenna systems is that matrix methods are used to process the measured data into an image. With such methods, small errors in the measurements or assumptions are enlarged during the processing by matrices. Other problems, such an ambiguous or inconclusive results, may occur with the computational matrix method itself.

More recently, two microwave methods have been proposed specifically to detect breast cancers. Both employ no more than a few narrow-band, fixed frequencies. One such method applies unfocused 900 megahertz energy directly to the breast via a resonant, open faced cavity applied directly to the breast. Some promising preliminary clinical results have been claimed if the data from adjacent breasts is compared. However, inconclusive results may occur in the vicinity of the nipple, where substantial variations in skin thicknesses occur. The other method proposes scanning a breast with a microwave beam via a dielectric slab pressed against the breast. The so-called beam of this method was relatively broad because it was developed by an open-ended wave guide pressed against the slab. The waveguide did not embody focusing features. As a result, reflections from many incidental scatterers not near a possible tumor could be expected. Such reflections could mask the desired returns. Further, it is nearly impossible to press such a plate uniformly against the breast without developing some air gaps that can cause massive reflections. Studies by the applicant demonstrate that the use of such a plate is disadvantageous and results in excessive reflections and reverberations from the skin that may mask any desired return.

The applicant's method is not like thermography, which uses the passive microwave or infrared emissions generated by malignant tumors which exhibit elevated temperatures with respect to normal breast tissue. Such radiated emissions must first pass through the normal breast tissue, then through the skin to a sensor placed on or external to the breast. Systems that have used such passive emissions have been clinically evaluated. A substantial number of analyses have been conducted, including a few that have considered but have not resolved the perturbing effects of the skin. The results are viewed as less efficacious than other detection modalities, such as X-ray mammography.

The applicant's method is also unlike hyperthermia methods that are designed to heat malignant tumors in situ, preferentially over normal breast tissues. Typically, an antenna or an array of antennas are placed near or over the breast. Fixed frequency, microwave energy generally below three GHz is then directed into the breast through the skin, through normal breast tissue and thence to the tumor. In some cases, electronically controllable phased arrays have been considered. The heating of the tumor has been optimized by invasively emplacing a sensor in the tumor; the sensor provides feedback signals to the electronic controls of the phased array to adjust the phase of each antenna for best results.

In summary, many, if not all of the past microwave methods, such as those used in thermography, hyperthermia or microwave imaging or detection, have experienced difficulties because breast tissues are not homogeneous; they are heterogeneous. A principal heterogeneity is associated with the skin, especially near the nipple. In addition, the dielectric parameters of the breast of one human may be significantly different than the dielectric parameters of other humans. Another problem is the necessity to focus the microwave energy into as small a spot or voxel as possible so as to be able to resolve very small tumors. This is best done by resorting to the smaller wavelengths of higher frequencies, frequencies well above those typically used for most of the reported therapeutic or imaging electromagnetic systems. However, such use of higher frequencies increases the difficulty of coping with skin-introduced heterogeneity effects.

The methods and apparatus described here envision an illuminator that propagates focused, short duration pulses of low power microwave beams into the breast or other tissues. The focusing may be effectively achieved either physically by lenses, reflectors, or phased arrays, or artificially by synthetic aperture methods. The pulses may be generated by pulse sources or synthetically by swept-frequency, Fourier inversion methods. When these effectively focused beams encounter a tumor, more energy is returned than from normal breast tissue. This occurs because a malignant tumor has significantly greater dielectric parameters than are exhibited by normal tissues. The backscatter returns from a possible tumor are captured by a collector that may also be effectively focused in the region of the expected tumor. By carefully focusing the power into a small volume or voxel within the breast and scanning the focal point from the skin to chest wall and from side to side, tumors can be detected and imaged.

Unwanted returns from heterogeneity in the breast are suppressed by several methods. One method is the use of a wide-aperture, confocal illuminator and collector. Typically, many of the features of the illuminator and collector may share the same position or function. Such a wide-aperture, con-focal design tends to average out minor variations in the dielectric parameters as well and to suppress returns from sources not near the focal point. Another method is to illuminate the breast or other tissues with short duration pulses, whether generated synthetically or in real time, to isolate the returns from scatters adjacent to a possible tumor and to compensate for propagation losses.

Specifically, the preferred apparatus of this invention employs short duration pulses (either in real time or synthetically generated) in combination with a multi-antenna array (either realized physically or synthetically). The perturbations introduced by the skin-related interfaces and any other heterogeneity in the breast or other tissue are detected and are used to suppress the unwanted effects of such perturbations. Such suppression may include a determination of the skin's thickness and its dielectric parameters. Another method uses electronically controllable phased or synthetic arrays. Such arrays, in combination with signal processing, can develop the approximate dielectric parameter of each breast or other tissue segment.

Such methods also can be used to determine whether or not a tumor is malignant or benign by noting the amplitude of the returns; malignant tumors usually exhibit much larger returns than benign tumors. All of the aforementioned techniques that are useful to suppress heterogeneity are also useful to help resolve whether tumors are benign or malignant.

SUMMARY OF THE INVENTION

One of the objectives of this invention is to mitigate the effects of heterogeneity in the breast or other tissues to allow both detection and imaging of very small, incipient tumors. This may be done by controlling the parameters of the electronic scanning to compensate for uncertain values of the dielectric constants in different portions of a breast or other tissue.

Another objective of this invention is to suppress the unwanted interface effects of the skin-to-normal tissue or skin-to-fat-muscle by gating out the transient responses caused by such interfaces.

Another objective of this invention is to determine the dielectric parameters of near-surface features, such as the skin, from measurements of the backscatter from selected apertures, and to use these dielectric parameters to modify the electronic scanning or signal processing to improve resolution.

Another objective of this invention is to provide a simplified method of electronic scanning that creates a synthetic aperture wherein the apparatus in the applicator is simplified and most of the phase shifting time delay and focusing is done analytically within the processing and imaging computer.

Another objective of this invention is to provide a simplified small aperture applicator to complement existing X-ray mammograms by distinguishing benign from malignant tumors and to assist in resolving ambiguous findings.

Another objective of this invention is to provide information on the size of prostate tumors so as to complement existing methods but with a different modality.

Another objective of this invention is to provide a simplified small aperture applicator suitable for determining whether or not a tumor in an animal, such as a tumor in the breast of a female dog, is benign or malignant.

Another objective of this invention is to use image processing methods that largely avoid the use of matrices which tend to enlarge small measurement errors or which result in ambiguous determinations.

BRIEF DESCRIPTION OF THE DRAWINGS

The following figures are used to explain the concepts and design of the invention as applied to microwave detection of cancers and other abnormalities in heterogeneous tissues:

in FIG. 7 the amplitude and phase of the backscattered signal is developed by means of a phase coherent detection method. Such characterization of the returns permits use of a frequency swept waveform that generates a synthetic pulse;

FIG. 21A, 21B and 21C are section detail views of the transrectal illuminator shown in FIG. 20.

DESCRIPTION OF THE PREFERRED EMBODIMENTS

The use of electromagnetic microwave or millimeter waves offers several advantages over x-ray mammography in detecting incipient breast cancers. (To simplify this discussion both microwave and millimeter wavelength regimes will be referred to as mm waves, or mmw.) Non-ionizing electromagnetic systems can be operated at sufficiently low levels so as to preclude biological hazards. A contrast ratio of the order of 20:1 is potentially usable for mm waves in tissue, whereas there is less than a few per cent range of densities for X-rays for soft tissue. The tissue-mm wave interaction also exhibits additional phenomena that can be drawn upon to enhance the performance. For example, when the diameter of a highly conducting sphere (e.g., an incipient cancer) is of the order of a wavelength in the breast tissue, a resonance effect occurs that increases the effective scattering cross-section of the tumor. If the tumor is non-spherical, then the polarization of the scattered waves may be different than that of the impinging waveform. In some cases, side-scattered or forward scattered energy can also be utilized. For purposes of this specification, tissue-mm waves are defined in terms of wavelength in a medium having a dielectric constant like that of breast tissue, not air. Thus, the operating frequency for an electromagnetic wave source used in the inventive system is preferably in the range of three to ninety GHz.

Other than the use of millimeter wave and microwave thermography to detect breast cancers, there has been little activity toward use of such mm wave approaches to detect breast cancers. As noted earlier, some of the problems that have to be overcome are formidable. First, simply flooding the torso of a female with mmw energy introduces numerous problems. How does one single out the scattered returns from a three millimeter circumference tumor from the immensely larger scattered returns from the torso? How is the defocusing effect of an air-skin interface overcome? Is the breast tissue sufficiently transparent, at mmw frequencies, to propagate energy into and out of the breast? Are the dielectric properties of the tumors sufficiently different from normal breast tissue for effective detection of small (e.g., three mm circumference) incipient cancers?

To understand the invention and its novel features, the basic concept will first be briefly described. Next, the ability of the millimeter wave electromagnetic energy to penetrate normal breast tissues will be demonstrated. Then, the special equipment and operating conditions will be described to realize the needed high resolution simultaneously with good penetration.

Figure 1A:
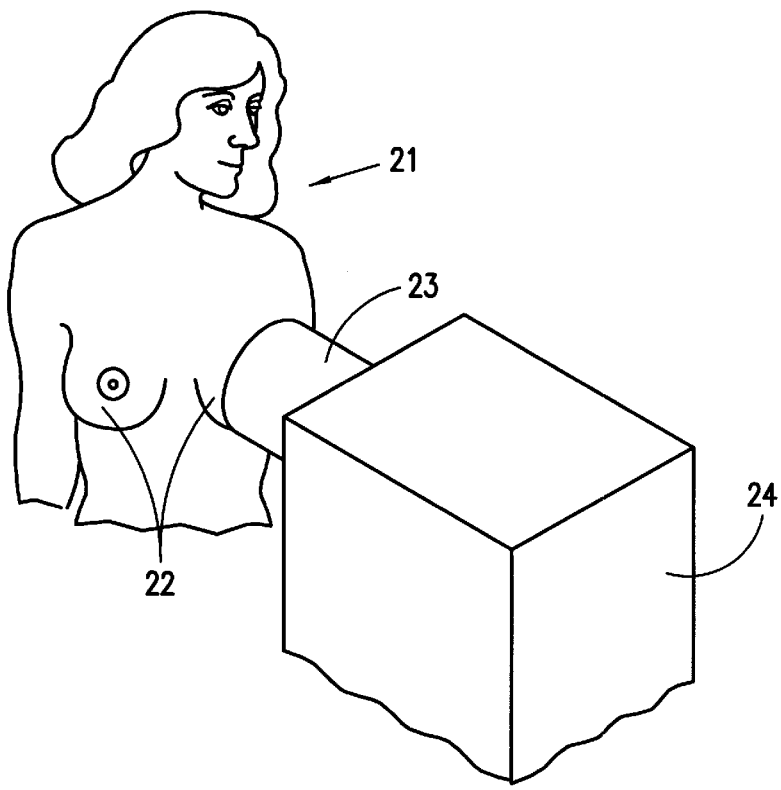
FIG. 1A, is a conceptual view of an active millimeter wave (microwave) breast cancer detection system, with a patient.
Figure 1B:
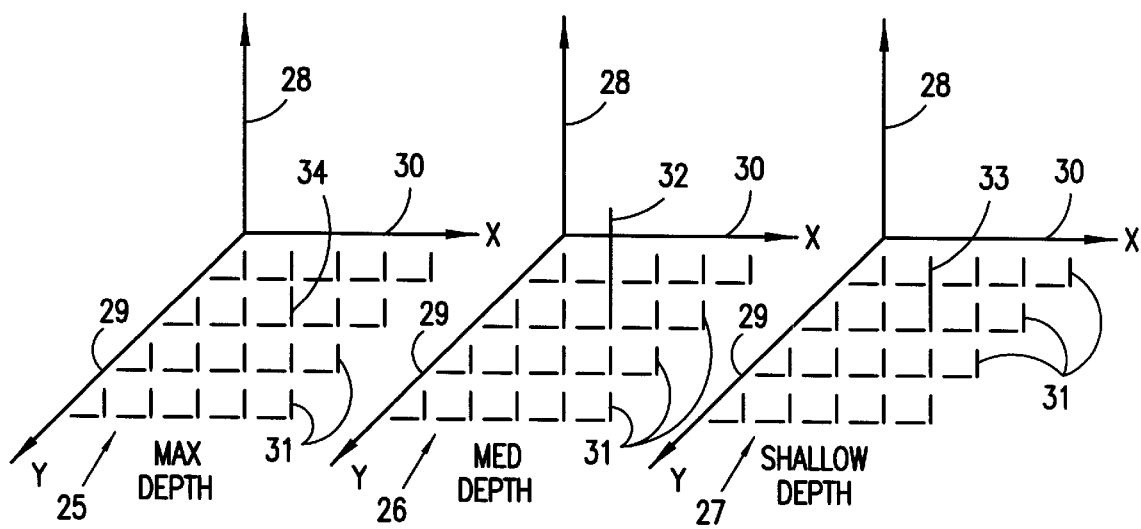
FIG. 1B illustrates displays for plural focal lengths, with the generalized system of FIG. 1A.

FIGS. 1A and 1B illustrate the basic concepts. FIG. 1A illustrates, on a conceptual basis, possible prototype equipment. The patient 21 arranges one of her breasts 22 to contact an illuminator 23 as shown. Mm waves are generated within the equipment housing 24. These mm waves are then propagated into the selected breast 22 as a refracted or reflected electromagnetic mm wave that is focused at a predetermined point or volume (voxel) within the breast. This is done by means of a unique combination of an interface and focusing apparatus, as described hereinafter. Further apparatus is used to cause the focal point of the beam to scan different small volumes or voxels within the breast. When this happens, the scattered mmw energy from any tumor present in the breast becomes much larger that other scattering sources, since the dielectric properties of a tumor are radically different those of normal breast tissue. The scattered returns may be collected as backscattered power via the same interface and focusing apparatus that is used to propagate the mmw power into the breast. The collected backscatter waves can then be processed by either analog or digital methods to form an image of the tumor.

A stepped FM sweep similar to pulse compression in "Chirp" radar to synthesize a time domain response to isolate shallow from in-depth scattering can be used to mitigate the effects of heterogeneity in the dielectric characteristic within the breast. A functional goal of the combined confocal and time-domain features of the present invention is to isolate the returns from tumors from spurious returns generated by heterogeneity in adjacent normal tissues.

The amount of collected backscattered energy and its time-of-flight or round trip time delay can be presented in a three dimensional format, as shown generally in FIG. 1B. For illustrative purposes, it is assumed that the impinging energy can be selectively and sharply focused into three vertical planes that are parallel to the patient's chest, wherein the X-Y planes at maximum depth 25, medium depth 26, and shallow depth 27 are shown. The three coordinates show the backscatter returns 28, the "X" coordinate 30 and the "Y" coordinate 29. Small vertical lines 31 are shown for numerous combinations of X and Y coordinates.

The amplitudes or heights of most of these lines 31 are proportional to the non-target returns that can arise from, for example, the tissues that surround the rib cage. Note that a large return 32 exists in the center of the medium depth display 26. This large return 32 is assumed to arise from a tumor that is at the focus of the impinging energy in the medium depth plane 26. In the center of the shallow plane 27 there is a somewhat smaller response 33 caused by a tumor intercepting and only scattering a small portion of the impinging beam. Note that in the center of the deeper plane 25, the return 34 is smaller because, it is assumed, the focused energy has largely been scattered by the tumor in the medium depth plane 26 before it arrives at the center of the deeper plane 25.

Figure 2:
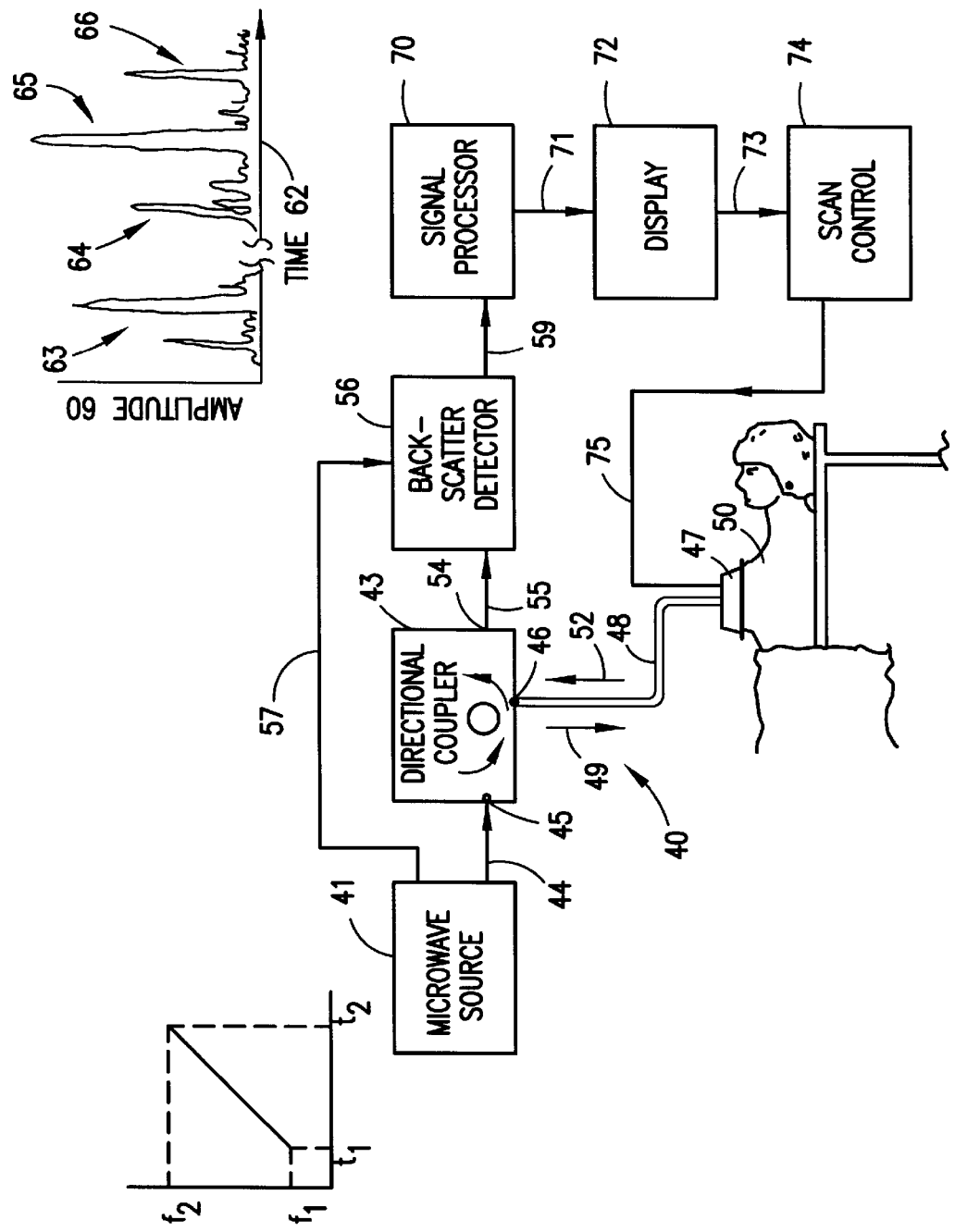
FIG. 2 is a simplified block diagram, with two supplemental charts, that illustrates the principal functions of a mmw breast cancer detection system constructed in accordance with the invention.

FIG. 2 illustrates the different functions that are employed to detect and image tumors in a system 40. A microwave or millimeter wave source 41 generates a frequency sweep as a linear function of time. Such a sweep can be processed to generate a synthetic pulse. This output power from the microwave source 41 is applied to an input port 45 of a directional coupler or circulator 43 via waveguide 44. The output power 49 from a port 46 of the circulator 43 is directed to an illumination/collector device 47 via a flexible waveguide 48.

The illumination/collector device 47, hereinafter called an illuminator, consists of an array of waveguides wherein the time delay of the power injected or collected by each guide can be electronically controlled or processed. The distal end serves as an antenna that both radiates and collects power. By electronically controlling or processing the time delay for each of the waveguides in illuminator 47, the power (arrow 49) that is applied to the illuminator 47 can be electronically focused into a preselected spot within the patient's breast 50. The illuminator 47, via electronic means, also collects backscattered power from the same focal point. Each antenna/waveguide can be connected to port 46 of the directional coupler 43 via the waveguide 48 and a waveguide switching arrangement, described hereafter, in the illuminator 47.

The requisite directing action of the directional coupler or circulator 43 can be realized by several "passive" means, such as a balanced bridge circuit or magic tee, a directional coupler, or a circulator (see Ramo et al. (1965) Fields and Waves in Communication Electronics, John Wiley and Sons, New York, sections 11.17, 11.8 and 9.16). "Active" means of separating the applied power of source 41 from the tumor-scattered power from illuminator/collector 47 are possible in the time domain. For example, very short duration pulses of mmw energy can be applied and the returns separated by time gating methods. Other "active" methods currently employed in some modern radar systems can be used, such as pulse compression, chirp or frequency modulation radar; see Skolnik, Introduction to Modern Radar Systems, McGraw-Hill (1980).

More detailed explanations are presented in subsequent portions of this application. When the radiation from the excited antenna/waveguide encounters a tumor, significantly more power is backscattered because the malignant tumor has a larger dielectric constant than the normal breast tissue adjacent the tumor. The backscattered power (arrow 52) from the tumor and other scatterers is collected by the excited antenna/waveguide in the illuminator 47. Via waveguide 48, the backscatter power from the excited antenna/waveguide is injected into the port 46 of the circulator 43. At the port 54 of the circulator 43, the collected backscatter power is separated from the input power that was applied to the port 45 by the unique properties of the circulator or directional coupler 43.

The output of port 54 is injected into a backscatter detector 56 via a waveguide 55. A portion of the swept-frequency mmw signal from the microwave source 41, is also applied, via a waveguide 57, to the back scatter detector 56. The backscatter detector 56 senses the amplitude of the backscatter power. The backscatter detector also ascertains the time of arrival of each of the amplitude components of the backscattered power by comparing the difference in the frequency of the power from the source 41 via cable 57 with a given amplitude component of the backscatter power from the tumor via waveguides 48 and 55. The greater the frequency difference, the further away the tumor is from the illuminator 47. The backscatter detector may also include means to compensate the returns for the attenuation and divergence experienced by the incident and scattered energy. By these or other well known radar techniques, such as FM Chirp or pulse compression radar, the "A Scope" display 60 shown in the upper right-hand corner of FIG. 2 is developed.

The time and the amplitude, in the "A scope" display 60, are developed from the returns from one of the waveguides in the illuminator. Equipment generated reflections 63, reflections 64 from the skin interface, reflections 65 from the tumor, and returns 66 from the chest wall are stored as real time responses in a signal processor 70, which is fed by a cable 59. Signals 63,64 and 66 are known and can be discarded by a time gating process in the signal processor 70, using data supplied from detector 56 by the cable 59. The tumor returns 65 are further isolated by a time-gating function in the signal processor 70; they are then stored in an imaging/display subsystem 72, fed via a cable 71 from the processor 70. A cable 73 supplies an output from display 72 to a scan control subsystem 74. Other antenna waveguides may be separately and sequentially connected to cable 48 by a switching arrangement in the illuminator 47. These are actuated by signals from the scan control subsystem 74, which is connected by a cable 75 to the illuminator subsystem 47. Additional time-amplitude displays 60 are developed and the related time-amplitude data is stored in the signal processor 70.

The signal processor 70 of FIG. 2 acts as an electronically controllable lens that is capable of positioning an apparent focal point anywhere within the breast 50 of the patient 51. Consider a round, spherical lens that is focusing sunlight into a spot. The focusing occurs, in part, because the on-axis rays that originate from the center of the lens are time-delayed more than the rays which are deflected from the circumference of the lens. The computer in processor 70 views each of the detected backscattered returns such as illustrated at 60 as one "ray". To obtain the potential backscatters for a scatterer that is, say, 30 mm below the center face of the illuminator 47, a similar process is employed. To each of the time-amplitude returns of display 60, a delay time is added. The most delay time is added to the returns from the waveguides (antennas) near the center of the face of the illuminator 47. Progressively less time delay is added, the further away the guides are from the center of the face of the illuminator. After the appropriate delays have been added to determine if a tumor is in a voxel 10 mm below the center of the illuminator 47, such delayed returns are summed together. If a scatterer or tumor is in the selected voxel, the scattered returns from the tumor add coherently. Other returns, such as from the skin or chest wall will not add coherently. This process is further described hereinafter.

Large returns, such as returns 63 from interfaces in the equipment or returns 64 from the skin, that might overload the dynamic range of the processor 70, can be gated out prior to summing. Further refinement is possible, such as compensating for the attenuation and dispersion of the observed responses as a function of time or distance from the antenna. If the propagation time is not well known, the delay times can be varied electronically in a manner that converges onto a best estimate. Another method is to develop the approximate depth and dielectric constant of the skin, so as to further enhance the accuracy and resolution.

Figure 6:
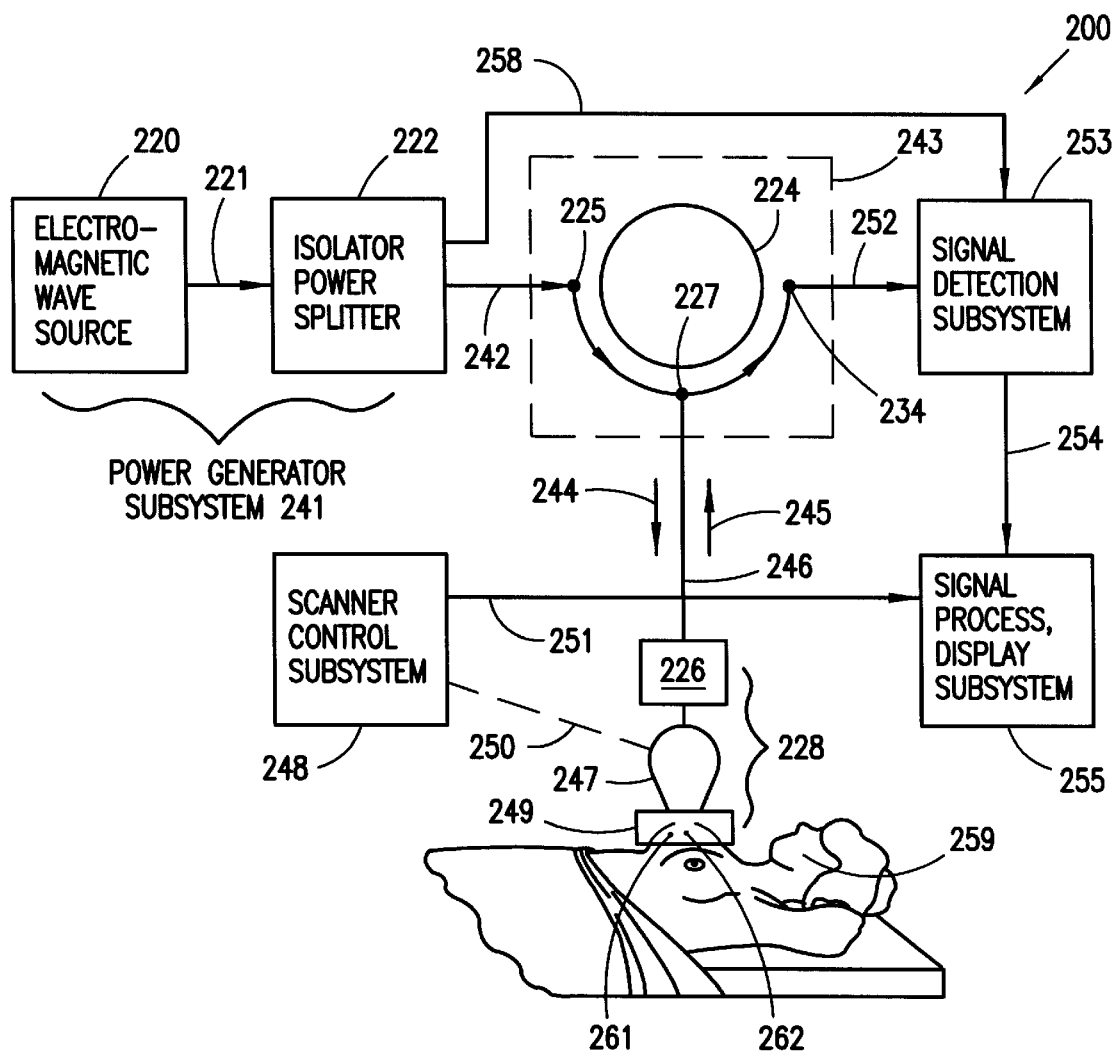
FIG. 6 is a block diagram of a mmw breast cancer detection system, according to the invention, that employs a "passive" signal separation technique in combination with a conventional heterodyne receiver to detect tumor-scattered returns.
Figure 7:
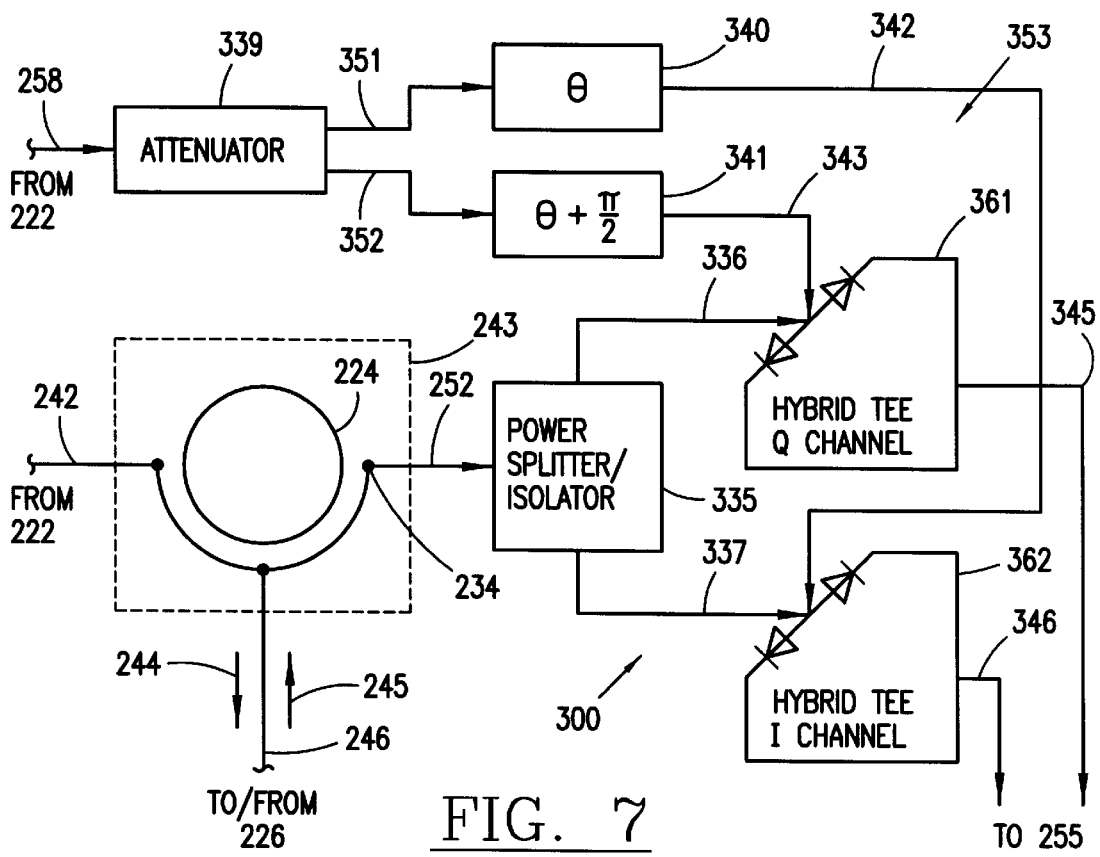
FIG. 7 is a block diagram of a breast cancer detection system that is a modification of the system shown in FIG. 6.
Figure 8:
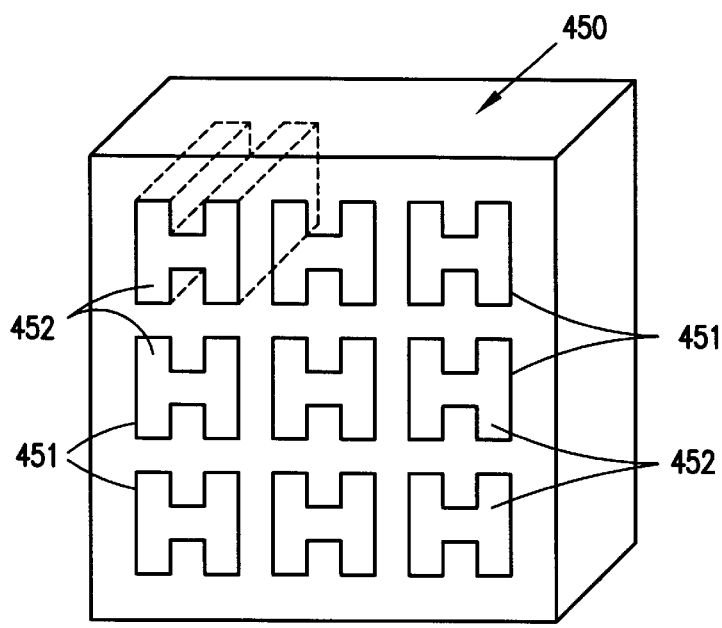
FIG. 8 presents a view of the face of an array of nine double-ridged waveguides that can be used as part of the illuminator in an electronically controllable phased array that is applied directly to a breast or other tissue.
Figure 9:
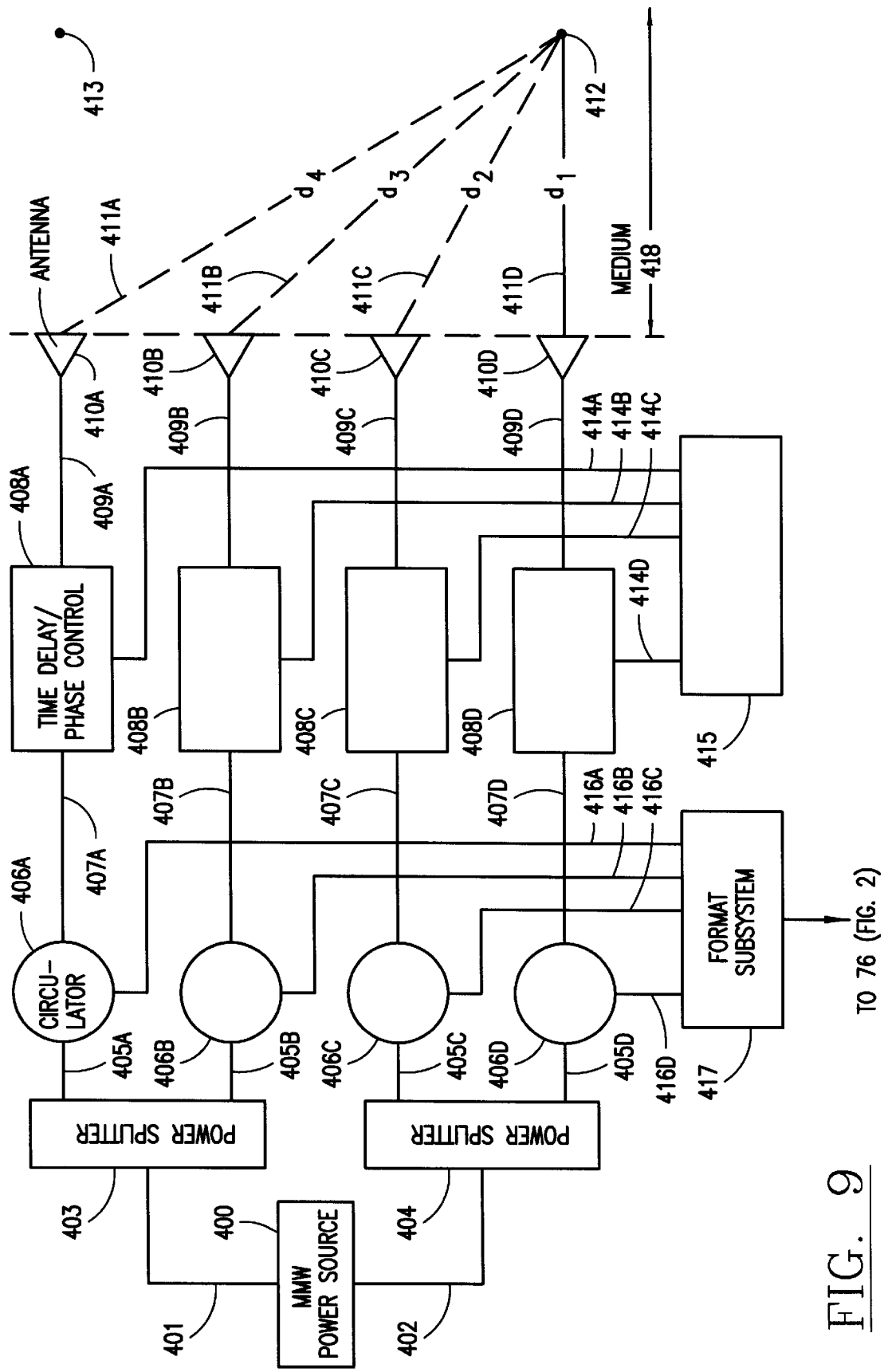
FIG. 9 illustrates the electronically controllable portion of an illuminator that employs phased array techniques.
Figure 10:
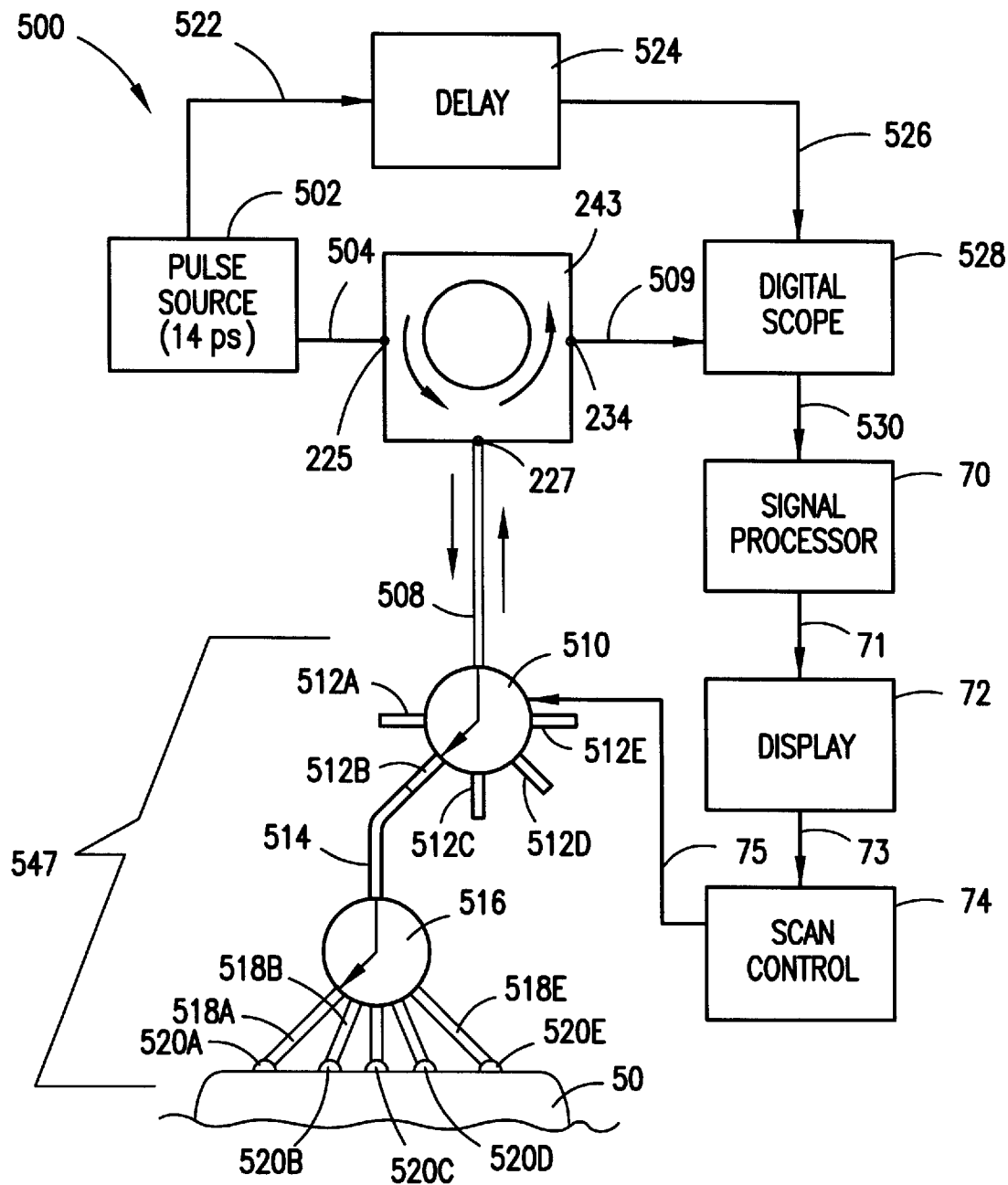
FIG. 10 illustrates how a source that generates very short duration pulses can be used to create a synthetic aperture that progressively excites each aperture afforded by an antenna array.

The system as discussed for FIG. 2 requires further explanation, especially regarding the applicator and electronic focusing features. Further discussion and means to compensate for heterogeneity of the breast will be made subsequently. To show that the breast tissue is reasonably translucent, published data on the dielectric properties of normal and malignant breast tissues will be discussed in connection with FIGS. 3, 4, and 5. FIGS. 6 and 7 provide further functional details of the microwave source 41, the directional coupler 43, and the backscatter detector 56. FIG. 8 illustrates a construction in which the faces of waveguides are emplaced in direct contact with the breast. FIG. 9 illustrates an electronically controllable illuminator that simultaneously excites the waveguides in the illuminator and that is best used with the synthetic pulse approach. FIG. 10 illustrates a system that generates and applies a pulse directly, rather than synthetically.

Figure 3:
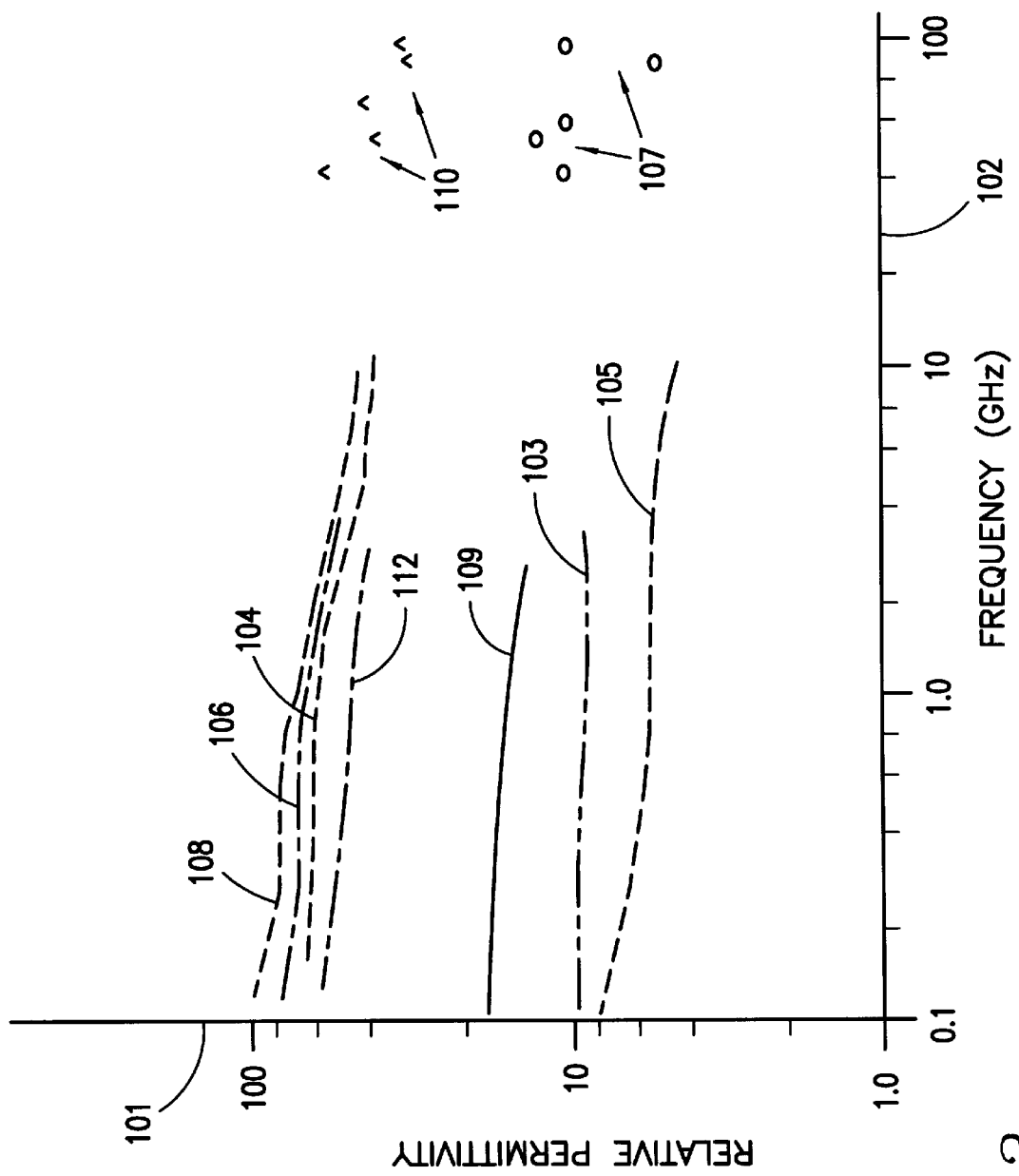
FIG. 3 is a graph of relative dielectric constants of muscle, fat, breast tissue and breast cancer as reported by various investigators.
Figure 4:
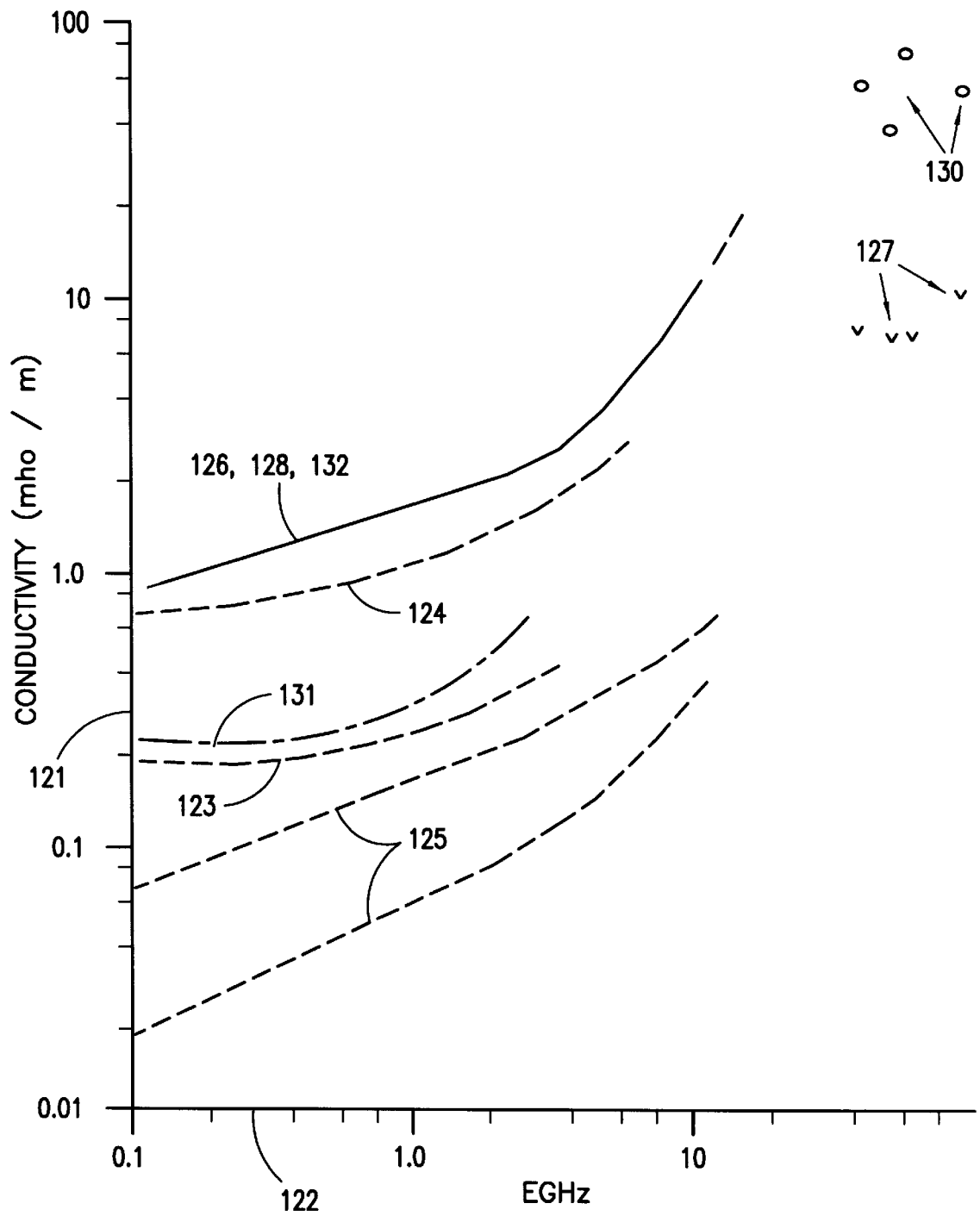
FIG. 4 is a graph of conductivity (mho/m) of muscle, fat, breast tissue and breast cancers as reported by various investigators.
Figure 5:
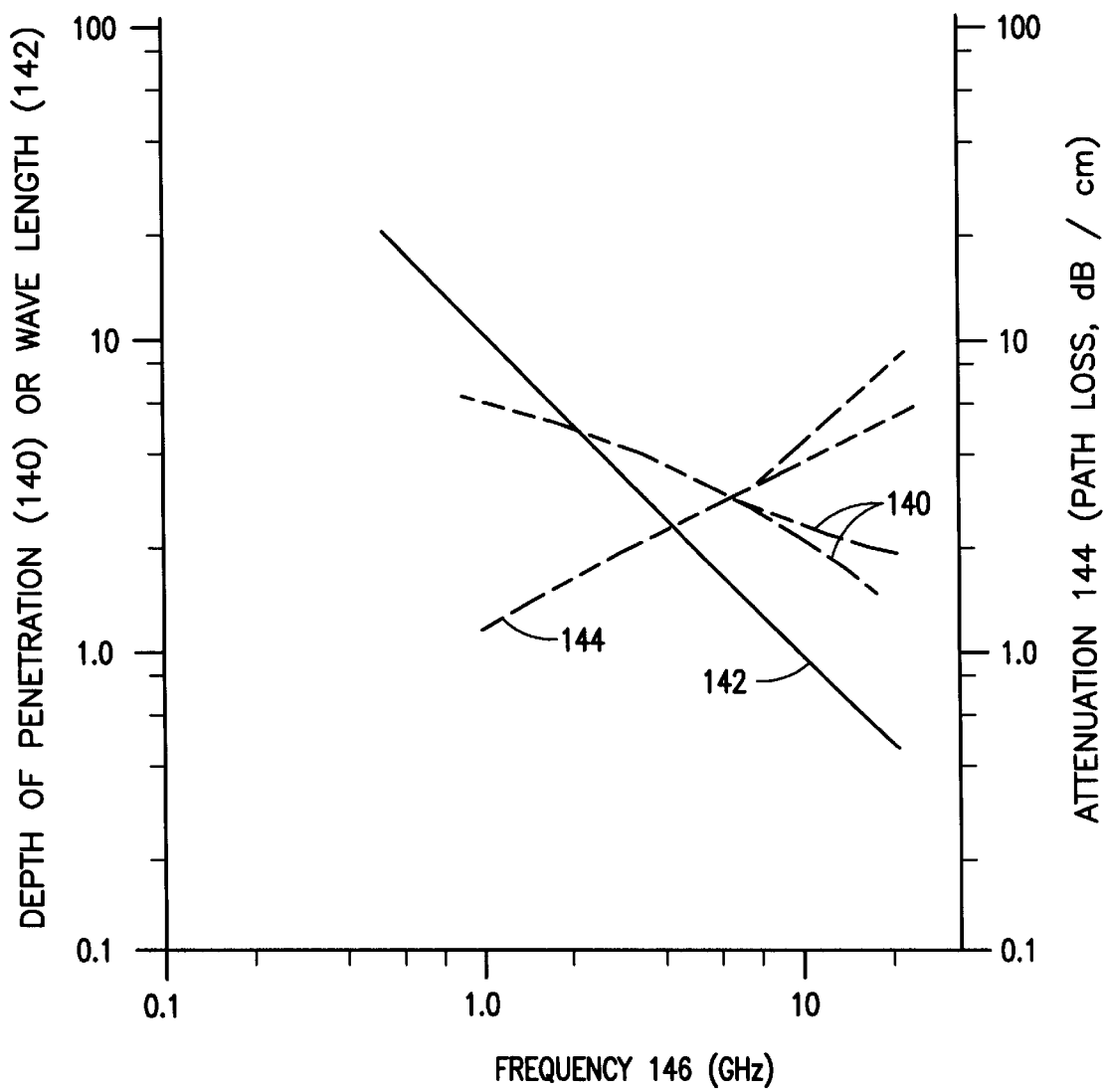
FIG. 5 is a graph of attenuation, wavelength, and depth of penetration in normal breast tissue as a function of frequency, based on the data presented in FIGS. 3 and 4.

FIGS. 3, 4 and 5 provide data that demonstrate that non-lactating breast tissue has different dielectric properties than either tumors or muscle tissues. Moreover, the attenuation of mm waves in such breast tissue is not excessive in the 5 to 15 GHz region and hence permits reasonable operating conditions for "passive" power and signal directors. Additional attenuation can be tolerated by the use of "active" power and signal directors such that operation up to sixty GHz is possible.

FIG. 3 summarizes data on relative permitivity, scale 101, as a function of frequency, scale 102. These data demonstrate that the relative dielectric properties of low-water-content tissues and normal breast tissues are significantly lower than for high-water-content tissues and tumors, either human or non-human. The low-water content data for curve 103 were developed by Chaudhary (1984) for human breast tumors. Johnson (1972) developed the data for curve 105 for fat, bone and low-water content tissue. Edrich (1976) generated the data for cattle fat, shown at 107. Burdette (1986) generated in vivo data for canine fat, illustrated in a curve 109. The high-water-content data for curve 104 was developed by Chaudhary (1984) for human breast tumors. Johnson (1972) developed data for muscle and high water content tissues, shown in a curve 106. Rogers (1983) generated the data, shown in a curve 108, for mouse tumors. Edrich (1986) collected data for canine muscle, illustrated at 110. Burdette (1986) provided in vivo data, shown in a curve 112, for canine muscle tissue. Note that in the case of muscle or tumor tissues, the relative dielectric constant is of the order of forty or more, depending on the frequency. In the case of low-water-content tissues, such as breast or fat, the dielectric constant is in the order of five to ten, as measured for in vitro studies. The in vivo measurement of Burdette (1986), shown in curve 109, shows an approximate increase by a factor of two in the relative permeability over the data developed by Johnson (1972), curve 105. The in vitro breast tissue measurements by Chaudhary (1984), curve 103, fall somewhat in between the in vitro values developed by Johnson (1972) and the in vivo measurements of Burdette (1986).

FIG. 4 presents similar data on the conductivity of both low and high-water-content tissues. The conductivity in mhos/meter, scale 121, is the ordinate and the frequency, curve 122, is the abscissa. The low-water-content tissues are human breast tissues, shown in a curve 123 derived from Chaudhary (1984). The low-water-content fat and bone of the curve 125 is from Johnson (1972). Cattle fat, shown at 127, is from Edrich (1986). The high-water-content tissues of the curve 124 are human breast tumors, data by Chaudhary (1984). High-water-content muscle tissue is in a curve 126, data by Johnson (1972). Mouse tumors, shown in a curve 128, are from Rogers (1983). Rat muscle data 130 is derived from Edrich (1986). Canine fat data are presented in a curve 131 from Burdette (1980), and canine muscle data in a curve 132 taken from Burdette 1980). Curves 126,128 and 132 are essentially coincident. Note that conductivity, as a function of frequency, tends to increase substantially above 6 GHz and that the 40 to 90 GHz measurements 127 and 130 of Edrich tend to fall in line with the trends established by measurement made up to 10 GHz.

Based on the data presented in FIGS. 2 and 3, FIG. 5 shows the depth of penetration 140, wavelength 142, and attenuation 144 as a function of frequency 146 for the propagation of millimeter waves in non-lactating breast tissue. Above ten GHz, some uncertainty associated with the trend extrapolation is suggested by the range of possible values of the penetration depth 140 or attenuation 144. A value of nine was used for the relative dielectric constant and the extrapolated values of Chaudhary (relative to the data developed by Johnson) from FIG. 4 were used for the conductivity. From these data, it is seen that the breast tissue behaves as a lossy dielectric for frequencies substantially exceeding five GHz, wherein $\omega=2\pi F$ and $\epsilon=\epsilon_o\epsilon_r$ (permitivity of free space)×(relative dielectric constant), $\sigma$ is the conductivity, $\mu$ is the permeability, f is the frequency, $\lambda$ is the wavelength, and $\delta$ is the depth of penetration (see Ramo (1965) page 334 Sec. 6.05).

Since $\omega\epsilon\gg\sigma$, the approximate lossy dielectric equations are as follows:

$$\lambda=(\mu\epsilon)^{-\frac{1}{2}} \qquad (1)$$

$$\delta=2[\sigma(\mu\epsilon)^{1/2}]^{-1} \qquad (2)$$

This defines the generic feasibility of the system to be described hereinafter. There are two requirements that must be met. First, the total path loss attenuation (in and out) should be substantially less than the dynamic range, typically in the order of 100 dB, wherein the dynamic range is defined in dB as equal to: 10 log[(largest signal power)/(smallest detectable signal power)]. Second, the wavelength in the irradiation apparatus (illuminator 47) and in the breast of the patient should be sufficiently small so that small tumors can be resolved. This, for the system discussed here, requires that, preferably, the wavelength in illuminator 47 and in the breast tissue should not exceed two or three times the circumference of the smallest tumor. If an operating frequency of 15 GHz is chosen for a passive power and signal detector, it is seen that the path loss is about 5 dB/cm, or 50 dB total path loss, in and out, for a 5 cm path length. The wavelength at 15 GHz is about 0.6 cm, which is about equal to the diameter of the smaller tumors.

As an introduction to some of the basic circuit functions, FIG. 6 illustrates a functional block diagram of a microwave breast cancer detection and imaging system 200 that employs a conventional heterodyne receiver. System 200 comprises the following subsystems: a millimeter power generator subsystem 241, a passive power and signal director 243, a focusing illuminator subsystem 228, a heterodyne receiver 253 employed for signal detection, a scanner control 248, and a signal processing and display subsystem 255. There is a connection 254 from the unit 253 to the display unit 255 and a connection 251 from the scan control 248 to the display unit 255.

Electromagnetic wave energy flows, via the power and signal director 243, from the power generation system 241 to the illuminator subsystem 228. The illuminator subsystem 228 includes features that physically or effectively focus, by synthetic methods, mmw energy into a voxel and electronic or mechanical features that allow the focal point to scan over a focal or voxel point 262 within the breast of a patient. The scanner control 248, through a mechanical connection or electrical cable, controls the location of the focal point 262 in three dimensions such that the focal point 262 is progressively positioned into each voxel (smallest volume element) of the breast under consideration. When the focal point encounters a tumor, the scattered returns are collected by the illuminator 247 of the subsystem 228 and then the scattered power (arrow 245) is supplied to the power and signal director 243 and then to the detection subsystem 253.

The scattered power 245 is separated from the impinging power 244 (supplied to the illuminator) by means of a directional coupler or circulator 224 within the power and signal director 243. A discussion of each of the aforementioned subsystems follows.

The power generation and control subsystem 241 is comprised of two functional blocks: an electromagnetic wave power source 220 connected via a cable 221 to an isolator and power splitter 222. This, in turn, is connected, via a cable 242, to the power input port 225 of the circulator 224 in the power and signal director 243. The power output and backscattered input port 227 of the circulator 224 is connected, via a cable 246, to the matching network 226 at the input of the illuminator subsystem 228. The output port 234 of the circulator 224 is connected to the signal processor subsystem 253 via a cable 252.

Many of the functions of these components are obvious. The isolator/power splitter 222 electrically isolates the power source 220 from any load variations that might be introduced by the circulator 224 or other components of the illuminator subsystem 228. The function of the circulator or directional coupler 224 is to extract the backscattered returns from the applied power. Otherwise, the high level of the power applied to the illuminator subsystem 228 would tend to overload the signal detector 253. Thus, the electromagnetic input signal injected into port 225 is directed out of port 227 and thence to illuminator 228. The backscattered returns that are applied to port 227 appear at port 234, wherein the amplitude of the applied power is greatly suppressed.

The performance requirements for the signal detection system 253 are not too stringent. The simplest version may use a simple heterodyne receiver as an RF voltmeter to measure the output of the circulator 224 at port 234. A reference signal from the power generation subsystem 241 can be supplied to the hetrodyne receiver 253 via a conductor 258 to stabilize the local oscillators in the receiver.

Other versions of the invention, such as the system 300 shown in FIG. 7, offer additional signal processing options. The system 300 of FIG. 7 illustrates the use of two synchronous receivers or detectors in a modification of the system of FIG. 6 in which only the signal detection subsystem is changed, with subsystem 253 of FIG. 6 replaced by a dual subsystem 353 that includes two hybrid tee synchronous detectors 361 and 362. The power splitter 222 (FIG. 6) provides a reference signal, on conductor 258 (FIG. 7) to system 353 as well as to the power and signal director 243. Each of the hybrid tee devices 361 and 362 forms a product between the applied input signal and the composite backscattered returns. However, one of the reference waveforms is shifted ninety degrees with respect to the other reference waveform; the following relationships result, where:

ω is the angular frequency of the millimeter waves;

θ is an arbitrary reference fixed phase angle;

λ is the wavelength;

χ is the electrical path length from the scatterer to the hybrid tee;

β is the propagation phase constant and $\beta=2\pi/\lambda$;

χβ is the accumulated phase shift.

The output from each of the hybrid tees 361 and 362 is the product of the returned, scattered waveform and the reference waveform. Considering just the low frequency components of such products, the output of each of the hybrid tees is as follows:

$$A \cos [\omega t+\theta-2\chi\beta]\cos [\omega t+\theta]=A/2[\cos (-2\chi\beta)+\text{high freq. component}] \quad (3)$$

$$A \cos [\omega t+\theta-2\chi\beta]\cos [\omega t+\theta-\pi/2]=A/2[\sin (-2\chi\beta)]+\text{high freq. component} \quad (4)$$

The dual receiver system depicted in FIG. 7 draws the reference waveforms from the isolator-power splitter 222 via cable 258 of FIG. 6. An attenuator-power splitter 339 is used to reduce the amplitude of the waveform presented to the two phase shifters 340 and 341 via appropriate cables or other conductors 352 and 351. The output waveform of phase shifter 341 is advanced or retarded ninety degrees relative to phase shifter 340 to provide the desired quadrature relationship. The quadrature reference waveforms from circuits 340 and 341 are applied, via cables 342 and 343, to the hybrid tees 362 and 361, respectively. The output of port 234 of the circulator 224 supplies the power from the backscattered returns, via cable 252, to a power splitter-isolator 335. This circuit 335 diverts the backscatter return signal equally into cables 336 and 337, thus supplying the backscatter signals to the hybrid tees 361 and 362, respectively. These tees 361 and 362 each form a product between the reference waveform (from conductors 343 and 342, respectively) and the backscatter signals (on lines 336 and 337, respectively). The low frequency output from these two devices 361 and 362, on cables 345 and 346, provides critical inputs to the signal processor and display subsystem 255 (FIG. 6). Other variations of the above technique may be used to improve the signal-to-noise ratio, such as modulating the reference waveforms with another frequency well above the highest frequency of interest in the detected backscattered return. This removes the output signal well away from the troublesome shot noise that occurs at very low frequencies.

The scanner control subsystems (74 in FIG. 2, 248 in FIG. 6) control how the breast of the patient is scanned. In the case of electronic scanning, FIG. 2, scanner control 74 controls the x and the Y positions by methods described in conjunction with FIGS. 9 an 10. The scanner control (74 or 248) is connected to the illuminator (47 or 247) and, via the display unit 72, to the signal processing unit (70 or 255) in each of the described systems of FIGS. 2 and 6. Other methods, particularly techniques that synthesize large aperture antennas, could also be used; see FIGS. 10–13 and 15, as described hereinafter.

In any of the described systems the signal processing and display subsystem (e.g., subsystem 255 in FIG. 6) can employ any number of processing or display methods so as to suitably display the scattered returns.

The parameters needed to determine the spot size (voxel size) are the diameter D of the antenna aperture, the focal distance R, the spot diameter d, and the wavelength of the millimeter wave in the media. See Kay (1966) and Smith (1966) for more complete development of relationships. The spot size becomes:

$$d=2R\ \lambda/D \quad (5)$$

As was noted earlier in regard to FIG. 5, reasonable penetration losses of about five dB/cm occur for wavelengths of the order of six mm. Thus, if tumors in the order of three mm in circumference are to be resolved, the beam width or effective spot size should not exceed the tumor circumference by much more than a factor of three. Preferably, for improved spatial resolution, the wavelength should not exceed the tumor circumference by a factor of three. To achieve a spot diameter of six mm, the ratio of the focal distance R to the aperture diameter D should be about 0.5.

Another design consideration is the depth of field Δ, as related to the aforementioned parameters and the apparent angle of resolution Φ. Thus the depth of field becomes:

$$\Delta=[R^2\Phi]/[D\pm R\Phi], \text{ where } \Phi=d/R \quad (6)$$

Again, to obtain good spatial discrimination, the focal distance R should be small compared to the aperture diameter D.

However, short focal lengths cannot be easily developed if the dielectric constant between the media that form an interface are greatly different. This would be the case if an attempt is made to propagate millimeter wave power in air and thence into the breast. As seen in FIG. 3, the dielectric constant of breast tissue is of the order of nine, and such a large value (relative to a value of one for air) causes substantial reflection and refraction of the incident power at the air-breast interface. More importantly, the apparent R/D ratio is reduced; that can lead to a radical increase in the spot size. This difficulty is mitigated by making the properties of dielectric materials within the illuminator similar to those for the human breast or skin and placing the illuminator directly on and in contact with the breast.

The foregoing can be better understood by referring to FIG. 8, which shows a nine aperture waveguide module 450. Nine double-ridged waveguides 451 are used. Each of these waveguides is filled with a dielectric material 452 that approximates the relative dielectric constant of either the normal breast tissue or of the skin. In the case of a screening system, only four waveguide apertures might be used. The combination of waveguide apertures is pressed directly against the breast. By proper timing or phasing of the signals to each of the waveguides 451, the focal point can be positioned within the breast without the need for mechanical movement.

FIG. 9 illustrates one way that the phase or timing of the signal applied to the waveguides may be controlled to position the focal point in a medium 418 which contains the aperture antennas 410A, 410B, 410C and 410D and focal points 412 and 413. For initial explanation, the thickness of the skin is neglected. A source 400 of microwave power applies equi-phased power via wave guides 401 and 402 to two power splitters 403 and 404. The outputs of the splitters are applied, via wave guides 405A, 405B, 405C and 405D, to the circulators or directional couplers 406A, 406B, 406C and 406D. The forward power through these devices is transferred via the guides 407A, 407B, 407C and 407D to the variable time delay or phase control devices 408A, 408B, 408C and 408D. The return power is transferred via wave guides 416A, 416B, 416C and 416D to a subsystem 417 that collects the returns in a format suitable for additional processing by subsystem 70 of FIG. 2. The time delay in each device 408 may be controlled by changing the magnetic field bias applied to a ferrite element within each of the devices. Such bias may be supplied via the cables 414A, 414B, 414C nd 414D from the time delay control subsystem 415. The outputs from wave guides 405 are controlled by the signal processing and display subsystem 72 of FIG. 2. Via wave guides 409A–409D, the time delayed or phased controlled power is supplied to the aperture antennas 410A–410D. A portion of the outputs from these antennas reaches the desired focal point 412 via pathways 411A, 411B, 411C and 411D. At point 412, the phases of the rays shown are nearly identical.

Assuming a time delay of $t_1$, $t_2$, etc. for each of the delay control elements 408 and path lengths (411) $d_1$, $d_2$, etc., then $t_1+d_1/v=d_4/v$ for constructive addition where v is the velocity of propagation in the medium 418. To meet this requirement, $t_1=(d_4-d_1)/v$. Other time delays can be calculated in the same way.

Other methods of control are possible by controlling the phase of the signals applied to each aperture instead of by the timing devices. In this case, the relative phase between the signals applied to apertures 411C and 411D can be redefined by noting the following, where $\omega$ is the radian frequency [$2\pi f$] and $\theta_{12}$ is the phase difference between 411C and 411D, such that $$\theta_{12}=\omega[t_2-t_1]. \tag{7}$$

The confocal arrangement permits the reflected or backscattered signals from voxel 412 to return by the same pathways as the applied wave form. These backscatter signals are collected by the aperture antennas 410 and progress back through the time delay devices 408 to the circulators 406. These, in turn, supply data on the backscatter returns to subsystem 417.

The discussion of FIG. 2 also covers use of the illuminator and focusing arrangements described above in combination with an "active" or time domain method of separating the applied power from the scattered power. Other such active or time domain methods utilize a "Chirp radar" to produce added resolution in depth and additional clutter suppression. At a center frequency of 15 GHz a Chirp radar with a swept frequency bandwidth in the order of 5 GHz and with phase correction for the dielectric behavior of the breast tissue could produce range cell resolutions of the order of 10 millimeters. Alternatively, sequences of very short duration bursts of 15 to 25 GHz waveforms should also provide isolation of the applied power from the backscattered power by time gating techniques. Burst durations in the order of 100 picoseconds will provide depth discrimination of the order of 10 to 20 millimeters. This added discrimination would not only discriminate the incident power, but also could suppress backscatter returns from the different dielectric interfaces, such as the skin or muscles around the rib cage.

Active methods are of particular interest because these methods may be functional with total path losses up to 100 dB. Such path losses might be difficult to overcome with a passive system, since it may be difficult to reduce clutter levels below 50 to 70 dB the applied power. Since some of the clutter can be reduced by considering only the returns in just one voxel, active systems might be viable over a wider dynamic range. Also, shorter wavelengths with greater resolution can be used, since active systems can accept greater path losses, possibly as much as might be experienced by a system with an operating frequency as high as 60 GHz.

Swept frequency methods can be considered. For example, an FM Chirp radar method that has been used in weapons detection systems effectively separates desired returns from those generated by system discontinuities. A version of this would be attractive in conjunction with the confocal illumination method to separate the effects of near surface discontinuities or hetrogeneities from the returns at greater depth. Linear FM pulse compression radar (PCR) techniques might also be considered. These have been described by Jacobi (7) for biological imaging applications. The theoretical resolution of a PCR is given by R=C/2B, where C is the is the velocity of propagation in the media, and B is bandwidth of the transmitted wave form. Assuming a mid-band frequency of 8 GHz, a 5 GHz sweep and a medium with a dielectric constant of nine, a range resolution of one cm is indicated. However, a 2.5 GHz sweep may be more readily realized and could produce an in-tissue resolution of two cm. To realize this performance, the FM sweep must be highly linear, a pulse compression filter developed for this application and the dispersion effects of the dielectric compensated.

A stepped or swept frequency input impedance Fourier inversion alternative exists. This option transforms data developed from the frequency domain measurements to the time domain via digital processing, thereby eliminating the need for a pulse compression filter. This can be implemented by using either the phased array of FIG. 9 or the synthetic aperture technique described hereinafter in connection with FIGS. 10–15. The output signals from the circuit shown in FIG. 7 on lines 346 and 345 can be viewed as a complex input impedance, $S(j\omega)$, at a radian frequency of $\omega$ ($\omega=2\pi f$) to the illuminator. As the frequency is stepped from a low frequency to a higher frequency, the complex input impedance for each frequency is stored in a digital computer. If the frequency is swept or stepped over a band similar to that noted for the PCR system, similar spatial resolutions can be realized. Via digital processing, the complex input impedance data can be used to develop the complex Fourier component for each stepped frequency. Using inverse Fourier transformation, this series of spectral components can be processed to develop the real time response to an applied pulse or step function. The transformed data is then in the form of an amplitude vs. time response, similar to a radar A scope display, as if an impulse or stepped function had been applied at port 234 of the circulator or directional coupler 224 in FIG. 7. Initially, as illustrated in FIG. 2, the returns from system discontinuities, such as from connectors and the interface with the antenna in the illuminator, will be displayed. Then, the reflections from the near-surface (e.g. skin) anomalies in the breast will be displayed, along with the reflections from the deeper anomalies occurring at the longer times. The stepped frequency option offers the opportunity to include a standard correction at each frequency increment for a typical dispersion characteristic for normal breast tissues and could also include compensation for other factors such as path loss or system dispersion in the ferrite phase shifters. Some of the more modern network analyzers include a built-in stepped or swept frequency to time domain processing option.

The underlying mathematical basis is as follows. The general Fourier transformations are:

$$s(j\omega) = \int_{-\infty}^{+\infty} F(f)e^{-j\omega t}dt \qquad (8)$$

$$F(f) = \frac{1}{2\pi} \int_{-\infty}^{+\infty} S(j\omega)e^{j\omega t}d\omega \qquad (9)$$

Where F(f) is the impulse or step response
S(jω) is the Fourier transformation of F(f)
ω=2πf, t is time.

FIG. 10 shows an alternative way of generating very short duration rise-time pulses. As opposed to the use of synthetic pulse techniques (FM pulse compression radar) to artificially generate the pulse, pulse sources and digital oscilloscopes are commercially available that can generate and resolve pulses with rise or fall times in the order of 14 picoseconds. Such suggests effective operating bandwidths of up to 50 GHz. The main limitation is that the dynamic range is more limited, in the order of 40 to 60 dB, unless mitigation measures are employed. In the case of the synthetic pulse method, commercially available network analyzers can replace and supplement the circuit functions illustrated in FIG. 7. These instruments can generate a synthetic pulse and yet have dynamic ranges better than 100 dB.

The functional block diagram of system 500 in FIG. 10 shows a combination of a 14 picosecond pulse source 502 that supplies pulses to a power/signal director or circulator 243 via a waveguide 504. In many digital oscilloscope test configurations, the signal director function 243 is just a passive three-way pad or power splitter. The pad equally divides the power applied from one port 225 to the other two ports 227 and 234, typically with a 6 dB loss from the injection port 225 to either of the two output ports. Because the power that is applied to the digital scope 528 through port 234, via a waveguide 509 cannot exceed a specified value to avoid overload or burnout, the power that can be applied to the illuminator 547 of system 500 will be similarly limited.

One solution is to continue to use the power/signal director function 243, such as illustrated in FIG. 6. Other devices, such as a directional coupler, could be used. These will suppress the power applied to the scope 528 by about 15 to 30 dB relative to the power applied to the illuminator 547, thereby increasing the level of backscatter returns that can be applied to the digital scope by about 15–30 dB. This improves the signal-to-noise ratio of the system. The signal-to-noise ratio can be further increased by time averaging successive backscatter returns from the same voxel. The improvement is proportional to the square root of the number of returns that are summed together.

The power/signal director 243 supplies power to the illuminator 547 and to the digital oscilloscope 528 and illuminator 547 via the waveguides 509 and 508 respectively. The illuminator 547 is comprised of two rotary waveguide switches 510 and 516 that provide a selectable, single path interconnection to any one of an array of twenty-five aperture antennas 520; only five antennas 520A through 520E are shown. Switch 510 directs power to any one of five switches like switch 516 via the waveguide terminals 512A through 512E. Switch 510 may be connected to any one of its five terminals in response to signals from the scan control 74 via cable 75; see FIG. 2. As illustrated, terminal 512B of switch 510 supplies power via a waveguide 514 to switch 516B. Other switches and related waveguides that connect to switch 510 are not shown. Switch 516, in response from signals from the scan control, may direct power into any one of five antenna apertures, 520A, 520B, 520C, 520D and 520E via the waveguides 518A through 518E. As shown, switch 516 is connected to the terminal of switch 516 that supplies power to antenna aperture 520B via waveguide 518B.

Each of the twenty-five aperture antennas 520 (only five shown) is excited sequentially, via the illustrated switches, from the power/signal director 243, and backscatter returns go to the digital scope 528 via waveguide 509. Scope 528 also receives a reference signal from source 502 via a connection 522, a delay circuit 524, and a further connector 526. That is, backscatter of tumors and other sources in the breast are collected by one antenna aperture at a time and, via the pad or circulator 243, are directed to the scope 528. The scope 528 displays and stores the backscattered returns as is suggested in the A scope display 60, FIG. 2. The scope 528 also supplies the data stored in the scope, via a cable 530, to the signal processing subsystem 70. This subsystem, if needed, can time average the returns as needed to improve the signal-to-noise ratio. It further electronically manipulates the time-history from each of the aperture antennas to form an image of the scatterers in a breast by means of the display subsystem 72.

FIGS. 11, 12, 13, 14 and 15 illustrate how the signal processor 70 of FIG. 10 can electronically manipulate the time-amplitude backscatter returns that may be simultaneously developed by the synthetic pulse system of FIGS. 2 and 7 in combination with the electronically controllable phased array of FIG. 9. In the case of the real-time pulse system of FIG. 10, FIGS. 11–15 also illustrate how the sequentially developed returns can be similarly manipulated.

Figure 11:
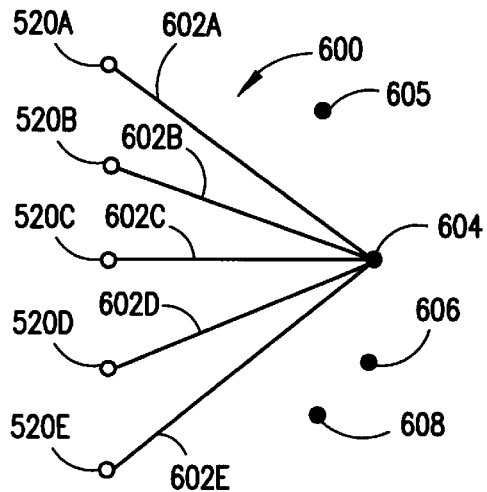
FIG. 11 is a time-of-flight diagram for five aperture antennas of an array that are focused on a voxel near the center of the array.
Figure 12:
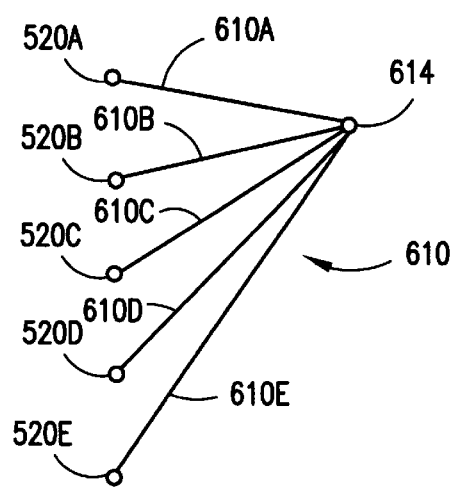
FIG. 12 is a time-of-flight diagram for five aperture antennas of an array that are focused on a voxel near one side of the array.

FIG. 11 is a round-trip, time-of-flight-distance diagram 600. Shown are the round-trip times-of-flight 602A through 602E for selected propagation pathways from the aperture antennas 520A through 520E. Assuming that the velocity of propagation is known, the length of the time of each flight line or pathway 602A–602E also represents twice the distance between the aperture antennas 520A–520E and a scatterer at a point (voxel) 604. FIG. 12 shows a similar time-of-flight distance diagram 610 for a different point (voxel) 614. Assuming that the velocity of propagation is known, each of the round-trip time-of-flight pathways 610A–610E also represents twice the distance from each of the aperture antennas 520A–520E to a different scatterer positioned at point 614.

Figure 13:
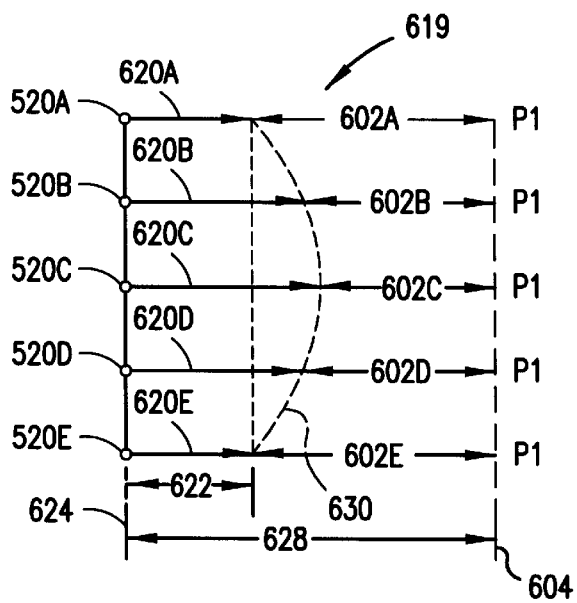
FIG. 13 is a diagram that illustrates how the times-of-flight of FIG. 11 can be processed by adding a predetermined time delay to the return from each of the antennas to enhance a returns from a center voxel.
Figure 14:
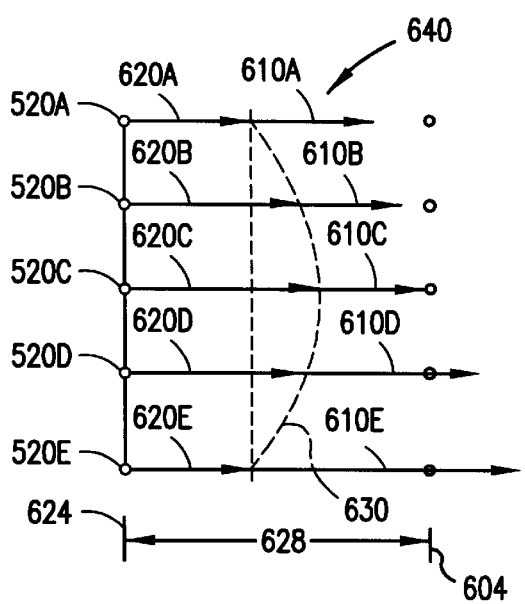
FIG. 14 is a diagram that illustrates how the times-of-flight of FIG. 12 can be used to suppress the returns from an off-center voxel by adding a predetermined time delay to the return from each of the antennas to suppress the returns from a voxel near one side of the array.

FIGS. 13 and 14 show how the observed round-trip time-of-flight data can be processed such that the returns from point 604 (FIG. 11 and FIG. 13) are enhanced and returns elsewhere, whereas returns from point 614 (FIGS. 12 and 14) are suppressed. On the assumption that the propagation velocity is known, the processor 70 (FIG. 2 or FIG. 10) selects a location or voxel, such as 604, and then adds a predetermined additional time 620A–620E (FIGS. 13 and 14) to the round-trip time histories of each of the backscatter returns. The time added, 620A through 620E, is equal to the estimated round-trip time-of-flight from the most distant aperture less the estimated round-trip time-of-flight from the nearest aperture plus a fixed buffer time 622. These estimated times are based on twice the distance between the aperture and the selected voxel divided by the assumed propagation velocity.

FIG. 13 presents data based on assuming the correct propagation velocity. Chart 619 of FIG. 13, beginning at time 624, presents lines whose lengths each include one of the predetermined additional times 620A–620E. These predetermined times are added linearly to the observed round-trip times 602A–602E as well as a fixed buffer time 622. If the propagation velocity is correctly chosen, the sum of the times (or line lengths in the chart 619, FIG. 13) will be equal to the interval 628 between the starting point 624 and the voxel point 604. When this occurs, the returns from the selected voxel 604 for each of the apertures add constructively, thereby suppressing returns from voxels not at the selected synthetic focal point.

FIG. 14 illustrates a chart 640 that is similar to chart 619, except the returns from voxel 614 (FIG. 12) are added to the estimated round-trip time-of-flights from voxel 604 (FIG. 11). The sum of these times (line lengths) are not equal. Some have small values, whereas others are greater. As a consequence, the returns from voxel 614 do not add constructively if estimated time-of-flights are based on the position of voxel 604. Note that the dash line 630 in FIGS. 13 and 14 has the cross-sectional configuration of a convex lens. In the case of a lens that focuses rays from the sun into a spot, there is just one focal point. To focus the lens at some other point, the lens must be moved, or its curvature altered. Likewise, the various estimated time delays 620A–620E must be changed to focus the synthetic lens other than at the position of voxel 604.

Figure 15:
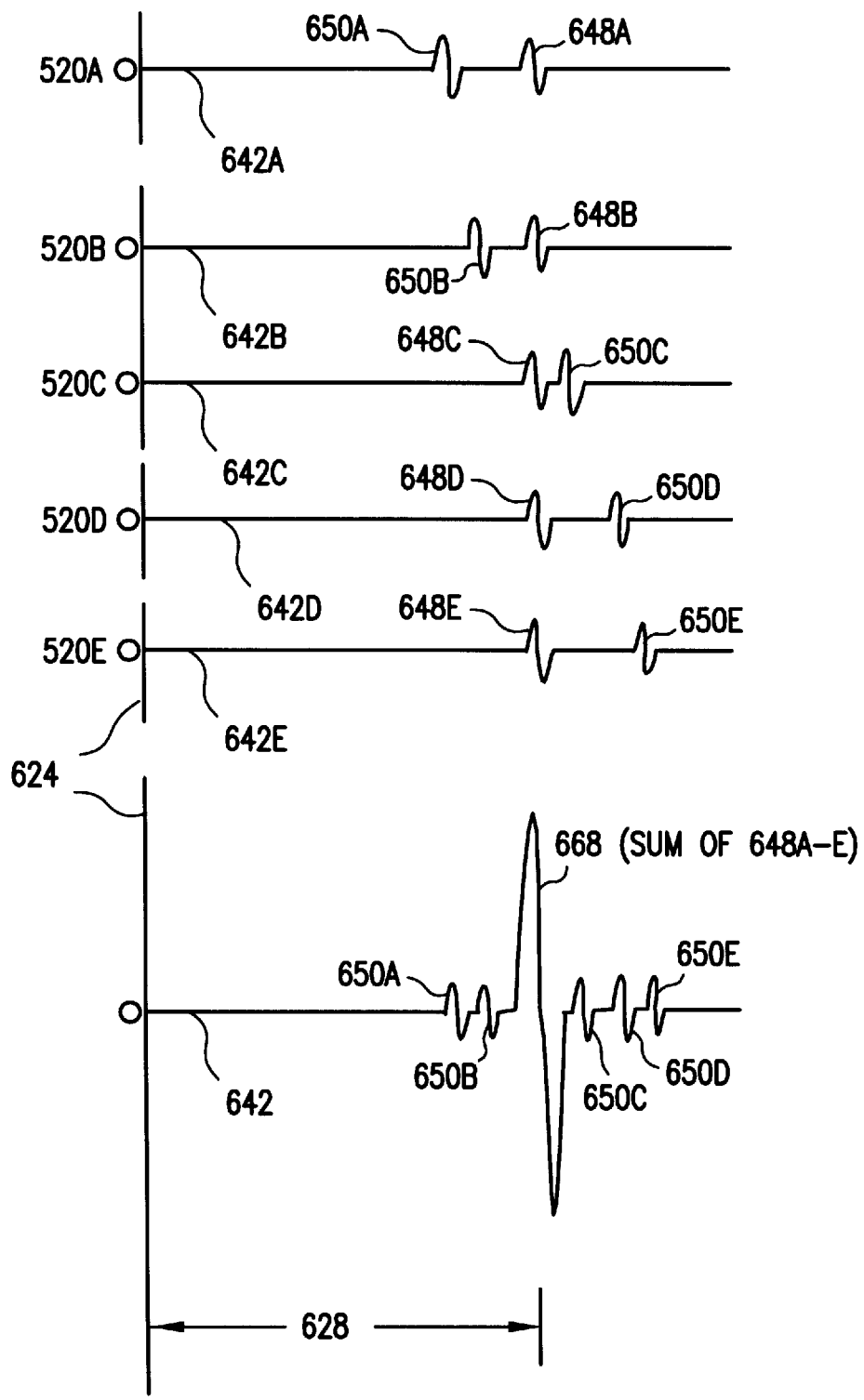
FIG. 15 illustrates how composite returns from a near center voxel and from an off-center voxel can be combined in real time to show how the returns from a voxel at the focus is enhanced over a voxel not near the focus.

FIG. 15 illustrates how the time histories of return (backscatter) signals from each of the antennas 520A through 520E can be combined to enhance the returns from the presumed tumor in the preselected voxel 604 over those from the nearby voxel 614, in the case where both voxels 604 and 614 are present; see FIGS. 11 and 12. For illustrative purposes, the return from the scatterer at each of the points 604 and 614 is assumed to be in the form of a one-cycle sine wave. It is also assumed that the path attenuation and divergence are normalized.

In FIG. 15, the time histories 642A through 642B for each of the antennas 520A through 520B, respectively, are shown at the top of the chart; the combined output of the antennas is illustrated by the curve 642 at the bottom of FIG. 15. Each time history is plotted as a function of time. The individual waveforms from the scatterer at point 604 (FIG. 11) are shown as single-cycle sine waves 648A through 648E, all of which are coincident in time. In a similar fashion, the waveforms from the scatterer at voxel 614 (FIG. 12) are shown as thhe single-cycle sine waves 650A through 650E, which are not coincident in time. See also FIGS. 13 and 14.

The curve 642 at the bottom of FIG. 15 summarizes the five individual time history curves 642A–642E. As before, curve 642 is plotted as a function of time, beginning at a time 624 taken as time zero. The returns 648A–648E (from voxel 604) all occur at about the same time, and coherently combine to afford a pulse 668 having an amplitude that is about five times greater than the amplitude of the return (648A–E) from each antenna. Because the returns 650A through 650E (from voxel 614) do not occur at the same time, and hence do not add coherently, they form a series of returns of smaller amplitude. These and the backscatter returns from other voxels are used to develop a three-dimensional image as suggested in FIG. 1B.

It cannot be assumed that the propagation velocity in the breasts of different women will be the same. One procedure would be to assume a likely overall average value and then observe the resulting images, especially for a known scatterer, such as the chest wall. Next, additional values for the overall average propagation can be selected and the resulting effect on image clarity noted, especially for known scatterers. Incremental changes in the propagation velocity should be changed in the direction that produces the greatest improvement. Such a procedure may lead to dithering the changes around a point of improved clarity or amplitude of returns. To fine tune the results, the propagation time from each aperture to a specific voxel, an interesting abnormality or regions of voxels can be changed or dithered, again initially choosing incremental changes in a direction that leads to the greatest improvement.

Recent studies conducted by the inventor demonstrate that the applicator-skin-breast tissue interface can introduce unexpected difficulties. The relative dielectric constant of the skin is in the order of 36 with a loss tangent of about 0.4 (as noted by Stuchly, 1980). The thickness of the skin of the breast can be expected to vary, with the most variation in the vicinity of the nipple. In addition, the skin of breast from different patients can also be expected to vary. The wave impedance of the skin is approximately one-half of that for the normal breast tissue. The velocity of propagation through the skin is also about one-half of that for normal breast tissue. The two-to-one difference in wave impedance results in substantial reflections. The slower velocity results in in-skin wavelengths in the order of 5 mm. Skin thicknesses as small as 1.2 mm can result in quarter wavelength transmission or reflection enhancements, depending on the nature of the interface. These effects tend to reduce the signal transmitted into and out of the normal breast tissues. In addition, reflections may tend to obscure the desired returns.

Methods and means are included here to overcome such difficulties. The reason is that the combined effect of both the thickness and the dielectric properties of the skin, especially the skin of the human breast around the nipple, has not been fully appreciated. This lack of appreciation is compounded because very little has been published on the dielectric properties of human skin.

It has been thought that the skin would not introduce a significant perturbation. However, simply matching the dielectric constant or wave impedance in the antennas within an illuminator to the dielectric constant or wave impedance of the normal breast tissue, or the skin of the breast, may not be adequate for high resolution and accurate imaging. On the other hand, if detection of just abnormalities is the goal for mass screening applications, such a consideration becomes less crucial and may possibly be ignored.

The methods described in connection with the systems depicted in FIGS. 2, 7, 9 and 10 indicate that the backscatter introduced by various interfaces, including that of the skin, could be made evident in the time-history of the backscattered returns. By so doing, the primary effect of the backscatter from the skin interfaces may be eliminated by gating or other processing. However, if more precision and resolution is needed, additional steps can be taken. One method would be to estimate the dielectric properties and thickness of each area of the skin that is in immediate contact with each aperture-antenna. The smaller wavelengths are used to help resolve the aperture-skin interface returns from the skin-breast/tissue interface returns. The reflection coefficients introduced at each of the aperture-skin interfaces are first developed. From such reflection data, the approximate dielectric properties, wave impedance, and propagation velocity within the skin can be estimated. The round-trip time between the aperture-skin and the skin-tissue interfaces can be determined from the time-history of the returns from each aperture. Knowing this round-trip time, the distance from the aperture-skin interface to the skin-breast/tissue interface can then be estimated. A possible next step would be to estimate the dielectric properties of the breast tissues voxels that are nearest to each of the apertures. This can be done by developing the reflection coefficient from the observed return from the skin-breast/tissue interface.

Figure 16:
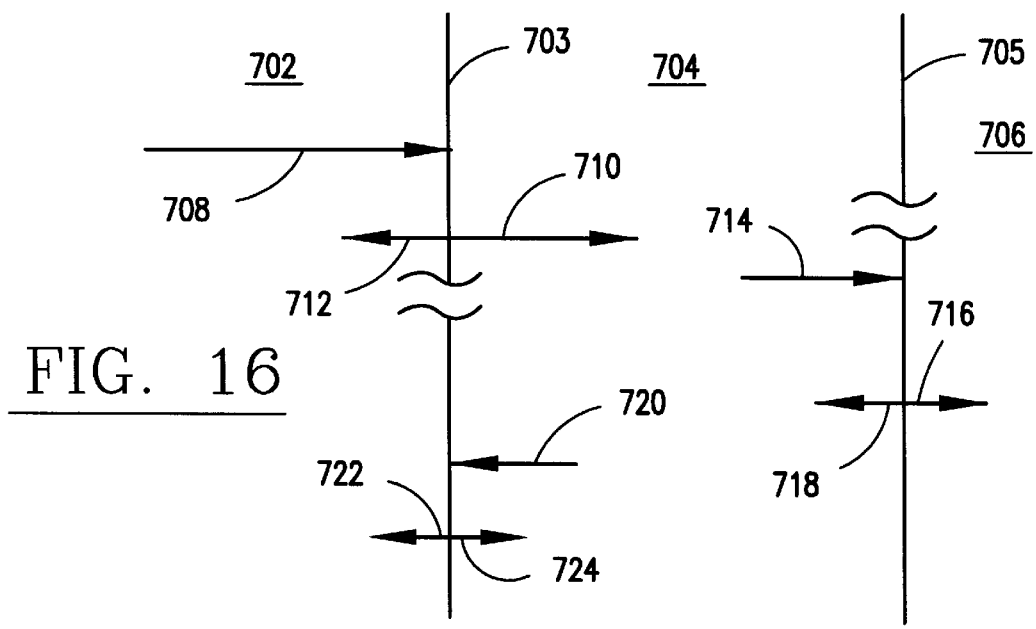
FIG. 16 illustrates the perturbations introduced by a layer of skin between a region near an antenna aperture and normal breast tissues for a propagating wave that impinges at right angles upon the surface of the skin.

This general method can be better understood by referring to the diagram 700, FIG. 16, which shows the aperture-skin interface 703 and skin-breast/tissue interface 705 between the dielectric or wave impedance properties within the aperture region 702, the skin region 704 and skin thickness 707, and the region of the normal breast tissue 706. FIG. 16 depicts the case for perpendicular incidence of an electromagnetic wave 708 that impinges upon the skin 703 of the breast from the aperture region 702. On encountering the interface 703, a reflected wave 712 and a transmitted wave 710 are produced. The transmitted wave 710 passes through the skin 704 and is partially attenuated, such that the remaining portion 714 encounters the skin-breast/tissue interface 705. As before, a reflected wave 718 and a transmitted wave 716 are produced. The reflected wave 718 returns back through the skin 704 such that the remaining attenuated portion 720 encounters the aperture-skin interface 703. As before a transmitted wave 722 and a reflected wave 724 are produced. The transmitted wave 722 is sensed by the aperture antenna and becomes part of the time-amplitude backscatter return.

To estimate the approximate dielectric properties of the skin, the reflection coefficient ρ, is the ratio of the amplitude of the reflected wave as noted in the time-amplitude return to the impinging wave (also known from calibration measurements) in terms of the wave impedance $n_1$ of the source region 702 (the aperture region).

The wave impedance of the adjacent skin region $n_2$ can be estimated as follows:

$$\rho = \frac{\epsilon(\text{reflected})}{\epsilon(\text{impinging})}, \text{ or} \quad (10)$$

See the prior text immediately preceeding equations (1) and (2).

The unknown value of $n_2$ may be estimated in terms of the known values of $n_1$ and ρ.

The transmission coefficient, τ, is the ratio of the transmitted wave to the impinging wave as follows $$\tau = (2n_2)/(n_2 + n_1) \quad (11)$$

from the calculated value of $n_2$ and the known value of $n_1$. Similarly, the transmitted and reflected waves at the other interfaces indicated in FIG. 16 can also be estimated and used to determine the approximate value of the dielectric parameters of the normal breast tissue near different specific apertures. See Ramo (1965, Chapter 6) for more complete discussions on reflection and transmission coefficients.

Figure 17:
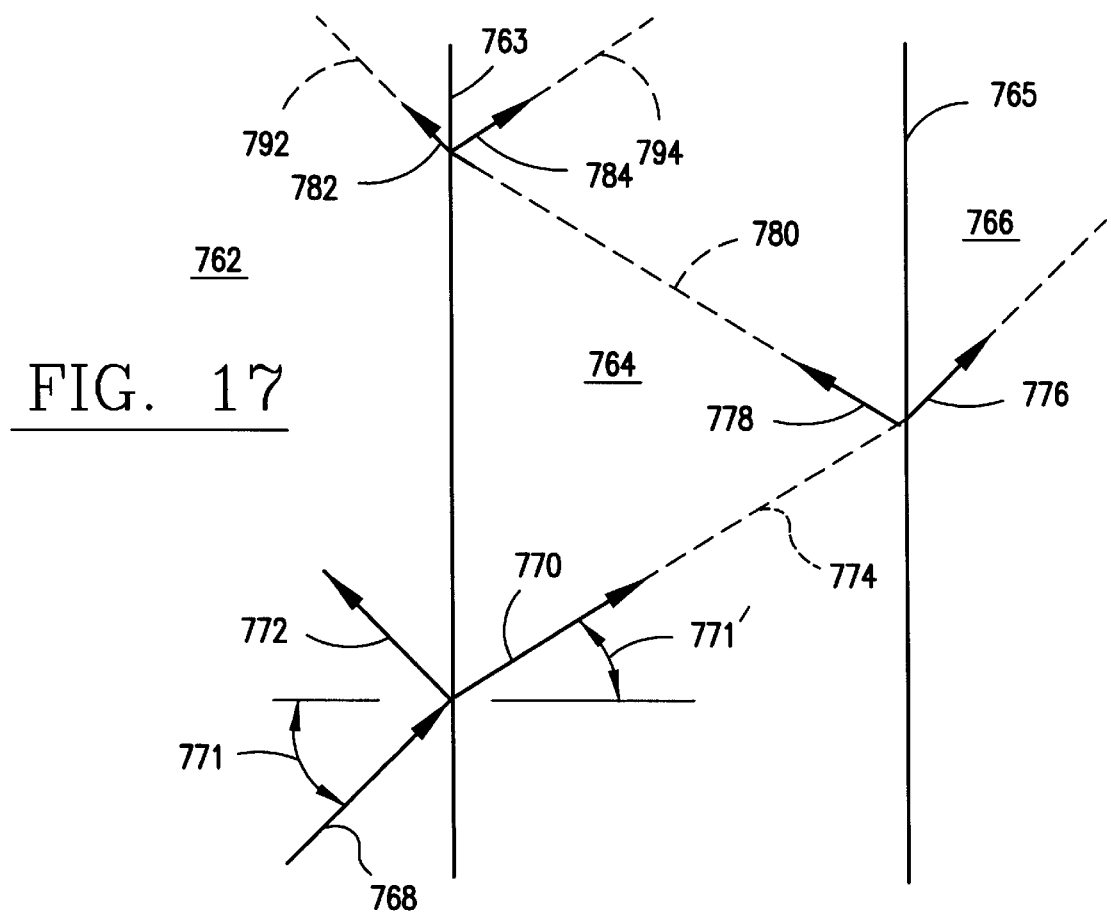
FIG. 17 illustrates the perturbation introduced by a layer of the skin between a region near an antenna aperture and normal breast tissues for a propagating wave that impinges at an acute angle with respect to the surface of the skin.

Knowledge of the dielectric parameters and thickness of the skin is helpful to compensate for refraction and reverberation effects that may be introduced from non-orthogonal propagation pathways. FIG. 17 illustrates the case where the impinging wave 768, in the plane of the paper, strikes the interface 763 at an angle 771. Media 762 and 766, corresponding to media 702 and 706 in FIG. 16, have a much smaller dielectric constant than the media 764 (704 in FIG. 16) that represents the skin. That is, the incident wave 768 strikes the interface 763 between media 762 and 764; the skin, medium 764, is assumed to have a much higher dielectric constant than the aperture region 762. A reflected ray 772 leaves the interface 763 at the same angle 771 to the normal to the surface that is formed by the incident ray 768. The transmitted ray 770, however, is refracted so that its angle 771' to the normal is smaller than the related angle 771 for the incident ray 768. The transmitted ray proceeds along the path 774 until the skin-breast tissue interface 765 is encountered. At interface 765, a reflected ray 778 and a transmitted ray 776 are formed. Reflected ray 778 proceeds along a path 780 until it encounters interface 763, where a reflected ray 784 and a refracted ray 782 are again developed and progress respectively along the paths 792 and 794. A key point is that the expected pathway of the incident wave 768 beyond interface 763, without accounting for the refraction effects of the skin, would be different than the actual pathway. In addition, reverberation effects within the skin layer may also occur.

The lossy dielectric approximation that is used above with equations (1) and (2), also applies for the foregoing interface relationships. This is justified because the measured (as published, Stuchly 1980) loss-tangent for skin is substantially less than one. Computer aided iterative approaches can be employed to develop more precise values. As the first step, the data developed by the aforementioned approximate lossy dielectric method is used. Then various values for the conductivity or dielectric constant are varied in an iterative manner. This is done until the best match between the theoretically predicted response (based on the best iterated estimate for the dielectric parameters) and measured response is realized.

Several different applications for the above discussed apparatus and methods are possible. If detection and imaging of the smallest incipient malignant tumors is desired, the number of antenna apertures should be large, the overall dimension of the array of the apertures should be large, and the greatest bandwidth, the highest possible frequency and the smallest rise time pulses should be used. These requirements are needed to assure high resolution and precise location. However, if the goal is just to detect an abnormality for mass screening, then the number of apertures can be reduced and the area of the array can be reduced. The maximum frequency and bandwidth can be reduced and longer rise time pulses can be tolerated.

To determine whether or not a palpable tumor is benign or malignant, the number of apertures can be reduced and the array can be reduced, to perhaps just one aperture. In such cases as this, the beam may be characterized as tubular, and the necessary information developed from a very short rise time pulse, from either a synthetic or a real time system.

Several types of aperture antennas can be considered. To take best advantage of the synthetic pulse or the real time step function or short duration pulse, a broad band radiating antenna is desirable. The abrupt termination of the double-ridge guides (FIG. 8) into high dielectric constant material, such as the skin of the human breast, may in some cases not produce the desired frequency response, especially at the lower frequencies. A broader band radiation structure is the tapered, dihedral horn 801 illustrated in the isometric view of FIG. 18. The overall arrangement of horn 801 comprises two conductive sheets 802 and 804 each constituting an isosceles triangle. The bases of these triangles are arranged to form an aperture 805 and the apexes are terminated near a position 807, with one sheet's apex connected to the plus phased point of a balanced feed waveguide 806 and other sheet's apex connected to the negative phased point of the balanced feed waveguide 806. A balun 808 converts the balanced system for coupling to the more commonly used unbalanced waveguide 810, such as a 3 mm diameter coaxial cable. The aperture antenna 801 can then be encapsulated in a gel or plastic that has the required dielectric properties to match either those for the skin or for the breast tissue. The dihedral arrangement shown in FIG. 18 can be used in an array configuration similar to that shown in FIG. 8.

Figure 19:
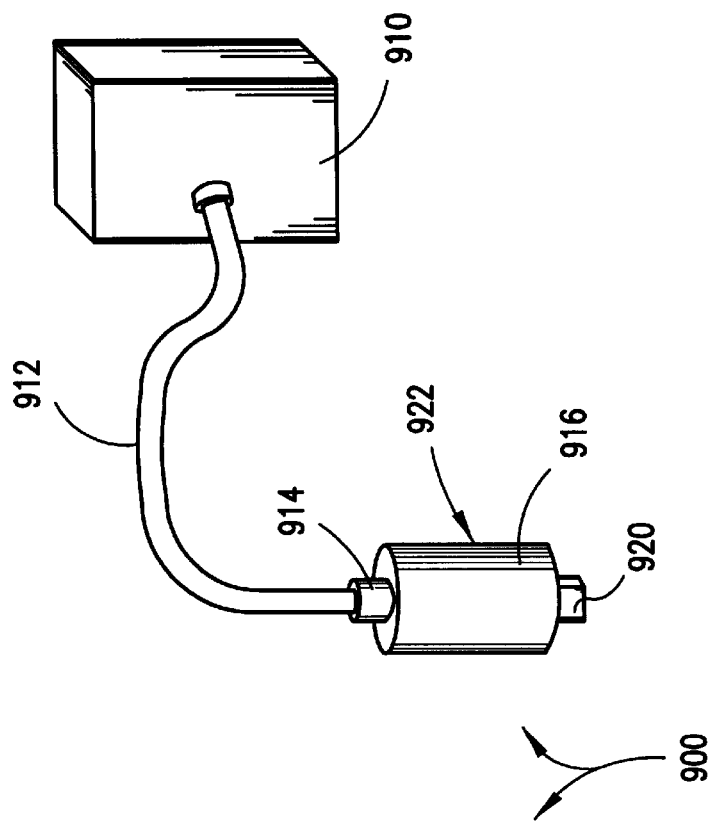
FIG. 19 illustrates simple apparatus that can be used to complement currently available tumor detection and location methods, such as to determine whether or not a tumor is benign or malignant.
Figure 18:
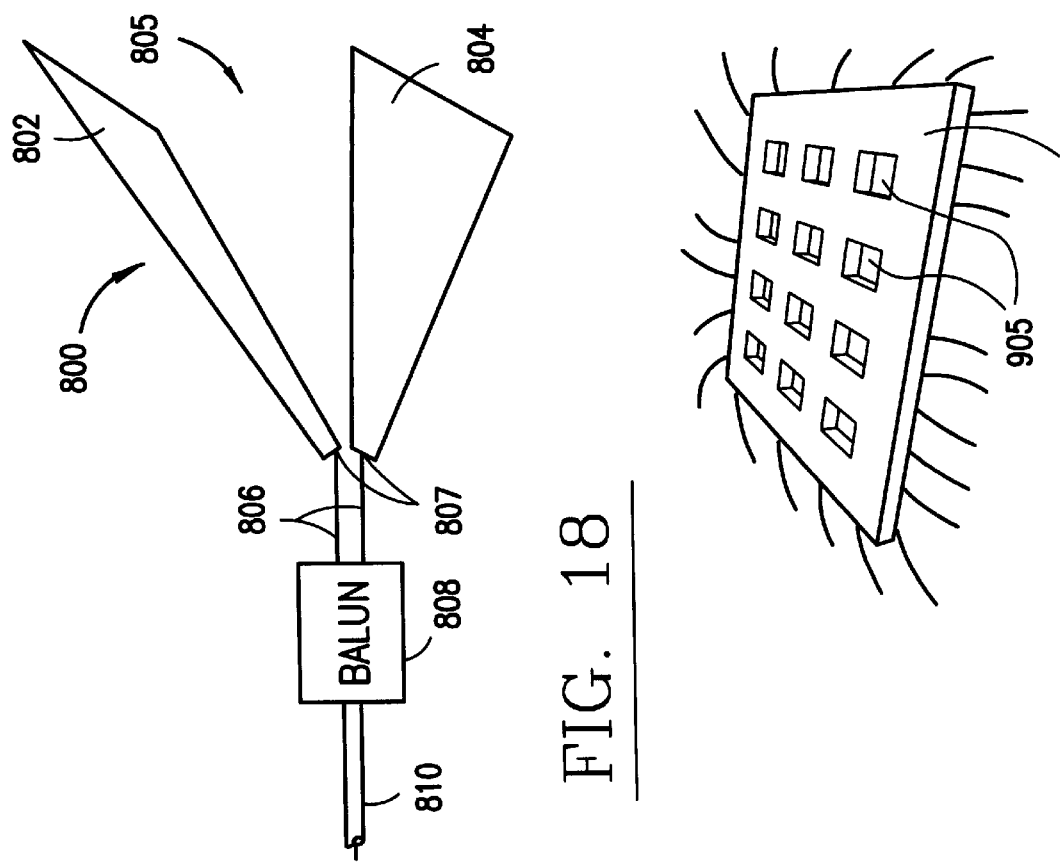
FIG. 18 illustrates a broad band aperture antenna.

FIG. 19 illustrates an apparatus 900 that may use the dihedral antenna of FIG. 18 (or an equivalent broad band antenna) for the purpose of determining whether a tumor that was detected by mammography or by palpation is benign or malignant. Precise imaging is not needed, and therefore the wide apertures and short focal length needed to develop a compact focal point may not be required. Fewer antennas may be needed, along with reduced overall size of the aperture. Such simplified arrangements could also be used to help resolve indeterminant images that are sometimes found in mammograms. In many cases, benign tumors contain less water than malignant tumors. Further, many benign tumors do not encourage the development of small blood vessels, such as those that usually surround a malignant tumor. The presence of blood vessels that surround a malignant tumor increases the backscatter, because blood has a high water content.

A non-conductive template 906 with plural slots 905 is placed on the breast 902 of a human or animal patient (not completely shown). The slots 905 of template 906, when contacting the breast, cause the skin of the breast to pucker up within each slot. The system 900 includes an illuminator 922 that contains a dihedral aperture antenna, such as illustrated in FIG. 18. The shape of the plastic molding 920 that contains the dihedral antenna is keyed to fit into the slots 905 in template 906 and to contact the skin of the breast firmly. The system 900 also includes a unit 910 that includes operating components similar to those shown in FIG. 2, including a microwave source, a directional coupler or equivalent, a backscatter detector, a signal processor, and a display. The system 900 of FIG. 19 is designed to detect the antenna-skin and the skin-tissue interfaces, as well as backscatter. The backscatter from each of the slots 905 in template 906 is measured by placing the illuminator 920 into each slot. The returns are stored and processed as described for FIGS. 10, 11, 12, 13, 14 and 15. The switching functions shown in FIG. 10 are replaced by manually moving the illuminator 922 to each slot position while at the same time noting which slot positions are employed. The material of template 906 should be a plastic or other material that has dielectric properties similar to those of skin or of normal breast tissue when a dihedral antenna, such as shown in FIG. 18, is used. Alternatively, the template 906 could be metal, if an aperture antenna such as shown in FIG. 8 is used.

Throughout the discussion of pulse-type systems, methods are also incorporated to suppress reverberation between interfaces within the system. Examples of the use of waveguides that are somewhat lossy include the waveguides 508 and 519 in FIG. 10 and the flexible waveguide or coaxial cable 912 of FIG. 19. In addition, lumped or distributed lossy or reactive elements can be located near or within system interfaces, such as the switches shown in FIG. 10, to further suppress unwanted returns from incidental interfaces. Further dielectric, electrical parameters of the material used for the waveguides or the mouths of the apertures can be progressively changed to suppress unwanted reflections or to change the radiation pattern of individual aperture antennas.

Other applications of the above described techniques are possible. For example, benign tumors can be distinguished from malignant tumors by noting the amplitude of the backscatter returns. The dielectric constant of malignant tumors is in the order of 40 to 55 whereas a lipoma (a generally benign tumor) has a dielectric constant in the order of 20 (Foster 1981).

Persons skilled in the art can also modify the above methods to measure selected volumes of human or animal bodies, such as to determine the thickness of the fat layer immediately beneath the skin. Alternatively, the methods may be used to detect tumors or other types of abnormalities that are embedded in muscle or other high water content tissue. The dielectric constant of normal muscle tissue is large, in the order of 40 to 50, and its conductivity is also large. This results in depths of penetration that are too small at frequencies suitable for penetrating breast tissues. As a consequence, the operating frequency must be reduced to the 1 GHz lower level as opposed to the approximately 3 GHz lower level noted for breast tissues. Fortunately, the wavelength at a given frequency in muscle is about one-half of that for a similar frequency in normal breast tissue.

Figure 20:
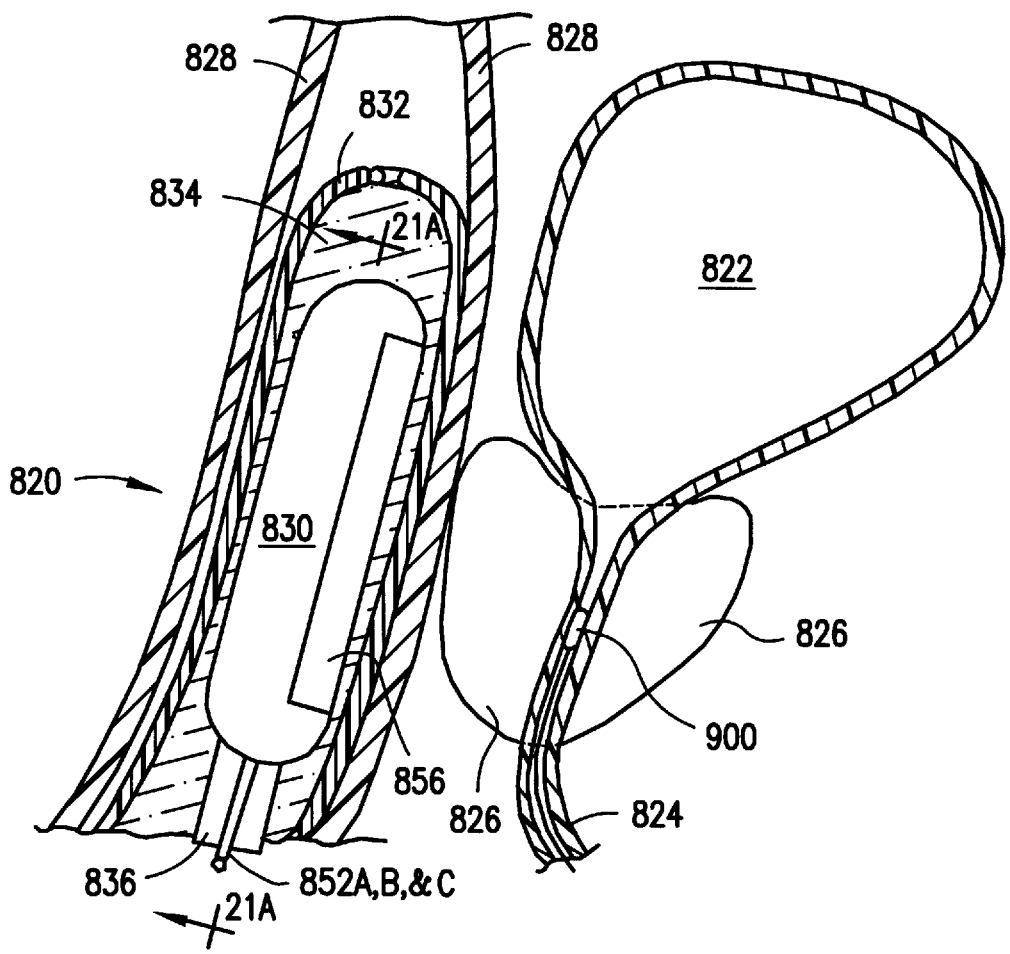
FIG. 20 illustrates a transrectal illuminator for a microwave detection and location system to complement existing prostrate cancer diagnostic methods.
Figure 22:
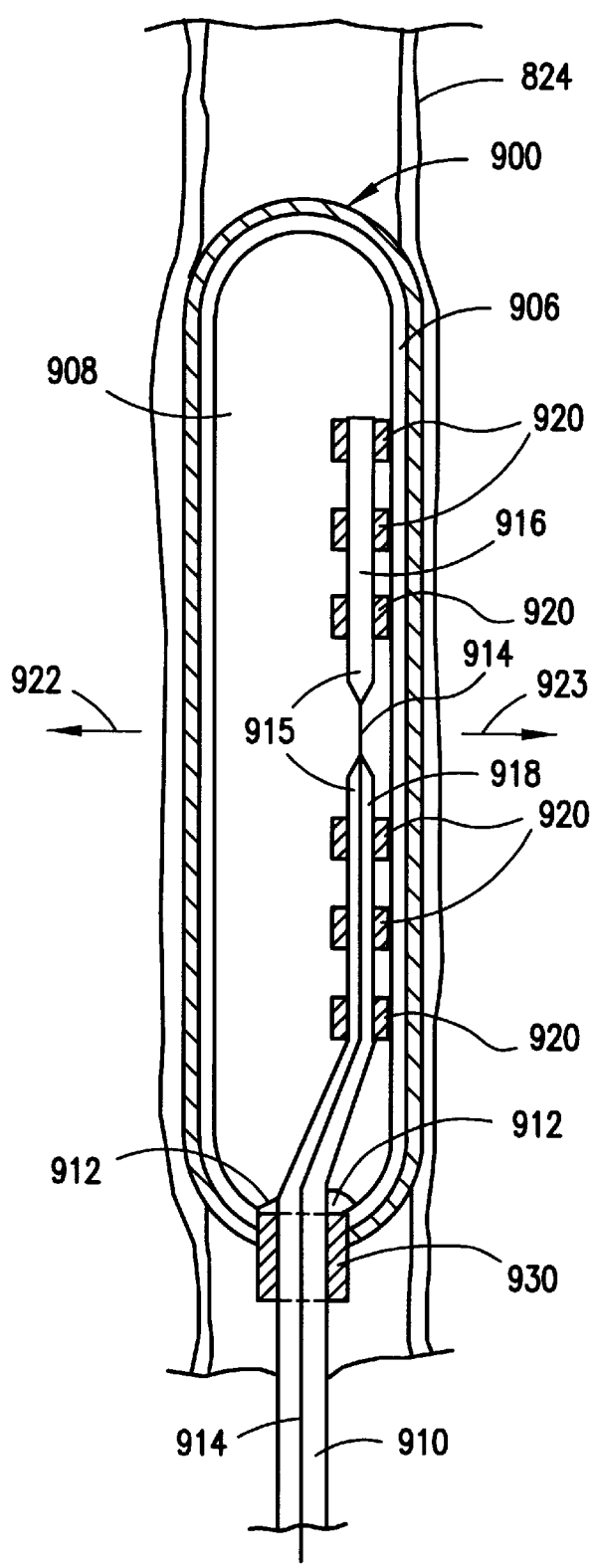
FIG. 22 is a detail view that illustrates a transurethral device shown in FIG. 20.

An important alternative application is to use the methods noted above to assess the overall volume of prostatic adenocarcinoma, because this volume is quite useful in developing a prognosis. Conventional digital rectal examinations are a poor predictor of cancer volume. Various techniques of transrectal ultrasound imaging have shown some promise, but the wide range of error usually prevents application to individual patients. PSA test levels have shown an excellent correlation but elevation produced by benign prostatic hyperplasia and advancing age renders the PSA unreliable for cancer volume prediction (Terris 1995). Of special interest are prostate cancer volumes in excess of about one to two cubic centimeters. FIGS. 20 and 21A–21C illustrate a transrectal application of the microwave methods noted here; FIGS. 20 and 22 illustrate a transurethral version.

FIG. 20 illustrates a transrectal arrangement 820. A cylindrical rectal insert container 830 is used to house an antenna array shown in FIGS. 21A–21C. The container 830 is surrounded by a fluid 834 that has a dielectric constant similar to that for the rectum wall 828. The balloon-like plastic film 832 that holds the fluid 834 is inflated after the container 830 is positioned in the rectum 828 opposite the prostate 826 by means of a cable assembly holder 836. The urethra 824 passes through the prostate 826 from the bladder 822. Also shown within the urethra 824 is a transurethral capsule 900 discussed later in connection with FIG. 22.

The section view of FIG. 21A, taken approximately along line 21A–21A in FIG. 20, faces the prostate 826. The wall of the capsule 830 may be metal or plastic, but the side wall 856 that faces the prostate should have a dielectric constant similar to that of the wall of the rectum 828. The capsule 830 contains a fluid 831 that has a dielectric constant similar to the dielectric constant for the wall of the rectum.

FIGS. 21A–21C illustrate the capsule 830 that houses antennas 850A, 850B and 850C. A plurality of dihedral aperture antennas (antennas 850A, 850B and 850C are shown) are positioned with their apertures facing side 856, as shown in FIG. 21B. Each of the antennas 850A–850C are supplied with microwave power, at their feed points 851A, 851B, and 851C, via twin-conductor shielded cables 852A, 852B and 852C. FIG. 21B illustrates a twin-conductor cable 852B connected to the feed point 851B of antenna 850B. A shield cable 852A is connected to antenna feed points 851A for antenna 850A; and cable 852C to antenna 850C. Capsule metal wall 830 and the partial dielectric (plastic) wall 856 are also shown.

Microwave power is applied to the cables 852A, 852B and 852C, FIGS. 21A, 21B and 21C, in a fashion similar to that noted for FIGS. 9 or 10. By following the procedures and processing concepts described for those figures, a crude focal point can be formed within the prostate 826 (FIG. 20) and used to develop a three dimensional scan. This should have sufficient resolution to detect cancers that have volumes greater than several cubic centimeters.

FIG. 22 illustrates the transurethral capsule 900 of FIG. 20. The capsule 900 is somewhat larger than the urethra 824 and is positioned in the urethra by pushing the capsule into the region of the urethra 824 adjacent the prostate 826 (FIG. 20) by means of a cable assembly holder 910. Within the capsule 900 there is a molded plastic bullet 908 that is smaller than the inside diameter of the capsule 900. The cable assembly holder 910 passes through a lubricator-gasket 930 and is attached to the bullet 908 the via braces 912. The space 906 between the bullet 908 and the capsule 904 is filled with a fluid that permits the bullet 908 to be rotated within the capsule by turning the cable assembly holder 910. Molded within the bullet 908 is the upper arm 916 and the lower arm 918 of a dipole 915. The dipole 915 is fed by the conductor 914 of a coaxial cable, whose outer conductor is also the lower arm 918 of the dipole 915. Three torodial ferrite cores 920 are positioned on each arm of the dipole 915.

The dielectric constants of the capsule 900 and the fluid in space 906 are similar to dielectric constant of the urethra or the prostate. The dielectric constant of the bullet 908 is about ten times greater than the dielectric constant of the capsule 904 and the fluid in space 906. For this arrangement, the radiation from the dipole 915 in the transverse or asmuthial direction will be maximum in the direction 922 and much smaller in the direction 923 (see Lytle, 1978). The ferrite toroidal cores 920 are chosen to cause the effective length of the dipole antenna to decrease as the frequency of the applied power is increased, thereby effectively increasing the bandwidth of the dipole antenna 915.

To develop a three dimensional image of the prostate, the capsule 900 is first positioned near the bottom of the prostate 826 in the urethra 824 (See FIG. 20). Microwave power is applied in the fashion noted for FIGS. 9 or 10 for a given angular orientation. Next the bullet 900 is progressively rotated in steps of about thirty degrees. For each step the returns are stored and processed as noted for either FIGS. 9 and 10. After completing a full rotation (in thirty degree steps), the capsule 900 is moved progressively further into the part of the urethra encompassed by the prostate such that at each position in the urethra, measurement of the returns for each angular position are taken and processed. By such a procedure, a crude image of the prostate and any possible cancers can be generated to estimate the volume of tumors larger than one to two cubic centimeters.

Throughout the foregoing discussion of pulse-type systems, methods are also incorporated to suppress reverberation between interfaces within the system. For example, waveguides that are somewhat lossy may be used, such as in the case of waveguides 508 and 519 in FIG. 10 or the flexible waveguide or coaxial cable 912 of FIG. 19. In addition, lumped or distributed elements can be located near or within system interfaces, such as the switches shown in FIG. 10, to further suppress the unwanted returns from such incidental interfaces. Further, electrical parameters of the material used for the wavegudies or the mouths of the apertures can be tapered (progressively changed) to suppress unwanted reflections or to change the radiation pattern of individual aperture antennas.

Throughout the foregoing specification and in the appended claims the terms millimeter waves, or mm, waves or mmw have been used to generically represent the wavelengths of the electromagnetic waves that propagate in the human breast tissue. Since the relative dielectric constant of the breast is in the order of 9 to 20, the free-space wave length will be reduced by a factor of three or more. Thus, the in-tissue wavelengths in the breast, over a frequency range of 2 to 60 GHz, will range from about 30 mm to 1 mm. For higher water content tissues, such as muscle, the frequency range is reduced by a factor of about three. In addition, the backscatter returns can be mathematically characterized in the time domain or the frequency domain.

As opposed to certain microwave hypothermia cancer treatment technology, none of the technology presented here is intended to heat significantly any portion of the breast. This requirement limits the power deposition density onto the surface of the breast to less than 10 milliwatts/cm$^2$ or the volumetric heating rate in any portion of the breast to less than 0.8 milliwatts per gram of tissue as averaged over a time period of about six minutes. To further assure minimal thermal effects, the input power is turned off if the scanning system falters for any reason.

Other usages are as follows: The term impedance refers to the ratio of the voltage to the current or to the electric field to the magnetic field at a specified location. This term impedance is qualified as "electrical" or "wave" respectively, depending on whether voltages and currents or electromagnetic fields are concerned. The term wave guide is used in the generic sense and includes both cables and higher mode wave guides with just a single transverse field. The terms effective aperture and effective focal point are used in the generic sense wherein apertures and focal points can be created physically or synthetically (such as often done in synthetic aperture radar).

The effective focal point is not a point but rather is defined here as a region where the illuminating energy is most concentrated in the breast. The effective focal point is further defined as the region or volume where this energy concentration occurs as affected by the heterogeneity of dielectric characteristics of the normal breast tissues, the in-tissue wavelength, the size and distance of the illuminating globular aperture or the geometry and number of apertures used in a phased array. The focal point positioning may be either mechanical or electronic as in the case of a phased array.

The terms "detect" or "detection" are also used in the generic sense, and may mean simply indicating the presence of a tumor or more broadly providing data that permits imaging the location, size and geometry of the tumor. Detecting, identifying, imaging or locating a tumor also means noting the presence of any abnormality. The terms "power and signal director" or "input power and signal separation" are also used in a generic sense. Both passive and active techniques not only enhance detection by suppressing the direct effects of impinging power waves, but also can reduce false signals or clutter. Such are introduced by imperfect matches between impedances or by non-tumor scattering sources, such as the breast/lung interface. In the appended claims, and in this specification, the term "time delay" includes phase delay unless otherwise indicated.

The following references are of utility in understanding the foregoing specification:

Burdette, E. C., et. al. (1980): In vivo measurement techniques for determining dielectric properties at VHF through microwave frequencies, IEEE Trans., MTT, Vol MTT-28, No. 4 April, pp. 414–427.

Burdette, E. C., et. al. (1986): In situ permitivity at microwave frequencies: perspective, techniques, results, medical applications of microwave imaging, Medical Applications of Microwave Imaging, Larsen, L. E. and J. H. Jacobi, IEEE Press pp. 13–40.

Chaudhary, S. S., et. al. (1984): Dielectric properties of normal and malignant human breast tissues at radiowave and microwave frequencies, Indian Journal of Biochemistry and Biophysiscs, Vol. 21, Feb. pp. 76–79.

Edrich, J., et. al. (1976): Complex permitivity and penetration depth of muscle and fat tissues between 40 and 90 GHz, (1976) IEEE Trans., MTT, vol. MTT-24, May pp 273–275.

Johnson, E. C., et. al. (1972): Nonionizing electromagnetic wave effects in biological materials and systems, Proceedings of the IEEE, Vol. 60, No. 6, June pp. 694–695.

Kay, A. F. (1966): Millimeter wave antennas, Proceedings of the IEEE, Vol. 54, No. 4, pp. 641–647.

Larson, E. E. and J. H. Jacobi, Eds. (1986): Medical Applications of Microwave Imaging, IEEE Press, Institute of Electrical and Electronic Engineers, New York.

Ramo, S., et. al. (1965): Fields and Waves in Communication Electronics, John Wiley and Sons, New York.

Rogers, J. A., et. al. (1983): The dielectric properties of normal and tumor mouse tissue between 50 MHz and 10 GHz, British Journal of Radiology, vol. 56, May, pp. 335–338.

Smith, W. J., (1966): Modern Optical Engineering, McGraw-Hill, New York, N.Y.

Stuchly, M. A. et. al. (1980): Dielectric properties of biological tissues, Journal of Microwave Power, 15(1), pp. 19–26.

Terris, M. K. et. al. (1995): Prediction of prostate cancer volume using prostate-specific antigen levels, transrectal ultrasound, and systematic sextant biopsies, Urology, Jan. Volume 45 No. 1 pp. 75–80.

Rogers, J. A. et. al. (1983): The dielectric properties of normal and tumour mouse tissue between 50 MHz and 10 GHz. The British Journal of Radiology, 56, pp. 335–338.

Foster, K. R. et. al. (1981) Dielectric properties of tumor and normal tissues at radio through microwave frequencies, Journal of Microwave Power, 16(2), pp. 107–119.

I claim:

1. A non-invasive method of detecting a presence of a tumor or other abnormality in the tissue of a living organism, such as the tissue of a human breast, wherein normal tissue has a predetermined dielectric characteristic different from the dielectric characteristic of a tumor or other abnormality, and wherein surface tissue such as skin has a different dielectric characteristic than the normal tissue, the method comprising:

A. generating a non-ionizing electromagnetic input wave within a preselected wide band frequency range;

B. applying the input wave of step A to a radiating antenna in contact with the skin of a living organism to illuminate a minute, discrete volume at a predetermined position within the tissue of the living organism and develop a backscatter wave from that volume;

C. collecting a preselected portion of the backscatter wave developed by step B with a collecting antenna in contact with the surface tissue of the living organism to develop a secondary backscatter wave that includes surface tissue backscatter; and D. processing the secondary backscatter wave of step C to separate surface tissue backscatter from the secondary backscatter wave and develop a segregated backscatter wave and detect an abnormality in the tissue.

2. A non-invasive method of detecting an abnormality in living tissue, according to claim 1, in which the radiating antenna of step B is also used as the collecting antenna of step C.

3. A non-invasive method of detecting an abnormality in living tissue, according to claim 1, in which, in step B, the input wave is applied to the radiating antenna through an input waveguide having a controllable time delay characteristic.

4. A non-invasive method of detecting an abnormality in living tissue, according to claim 1, and including the following step:

C1. delaying the second backscatter wave prior to processing in step D.

5. A non-invasive method of detecting an abnormality in living tissue, according to claim 4, and including the following steps:

E. repeating steps B, C, C1 and D for a second minute, discrete volume within the tissue of the organism.

6. A non-invasive method of detecting an abnormality in living tissue, according to claim 5, and including the following steps:

F. applying additional time delay to the segregated backscatter waves of steps D;

G. combining the delayed backscatter waves of step F; and

H. varying a time delay of at least one of the previous method steps to enhance the backscatter waves.

7. A non-invasive method of detecting an abnormality in living tissue, according to claim 6, in which, in step G, phase characteristics are varied to control time delay.

8. A non-invasive method of detecting an abnormality in living tissue, according to claim 1, in which, in step C, the collecting antenna is connected to a return waveguide having a controllable time delay characteristic.

9. A non-invasive method of detecting a presence of a tumor or other abnormality in the tissue of a living organism, such as the tissue of a human breast, wherein normal tissue has a predetermined dielectric characteristic different from the dielectric characteristic of a tumor or other abnormality or other tissue types, and wherein surface tissue, such as skin and other near-surface tissue, have a different dielectric characteristic than the normal tissue, the method comprising:

I. generating a non-ionizing electromagnetic input wave within a preselected wide band frequency range;

J. applying the input wave of step I to a radiating antenna in contact with the skin of a living organism to illuminate an adjacent small volume of the near-surface tissues within the living organism and develop a scattered wave from that volume;

K. collecting a preselected portion of the scattered wave developed in step J with a collecting antenna in contact with the near-surface tissue of the living organism to develop a secondary scattered wave;

L. processing the secondary scattered wave of step K to develop a dielectric characterization of the near-surface tissue; and M. utilizing the dielectric characterization of the near-surface tissues from step L to compensate for perturbations introduced into scattered returns by the near-surface tissues and detect an abnormality in the tissue.

10. A non-invasive method of detecting an abnormality in living tissue, according to claim 9, in which the radiating antenna of step J is also used as the collecting antenna of step K.

11. A non-invasive method of detecting the presence of an abnormality in the tissue of a living organism, according to claim 9, in which the near-surface tissue, in steps K, L and M, is the skin.

12. A non-invasive method of detecting the presence of an abnormality in the tissue of a living organism, according to claim 9, in which the near-surface tissue, in steps K, L and M, is the skin and adjacent normal tissue.

13. A non-invasive method of detecting a presence of a tumor or other abnormality in the tissue of a living organism, such as the tissue of a human breast, wherein normal tissue has a predetermined dielectric characteristic different from the dielectric characteristic of a tumor or other abnormality or other tissue types, and wherein surface tissue, such as skin, has a different dielectric characteristic than the normal tissue, the method comprising:

N. generating a non-ionizing electromagnetic input wave within a preselected wide band frequency range;

O. applying the input wave of step A to an array of radiating antennas in contact with the surface of a living organism to illuminate minute, discrete volumes at predetermined positions within the tissue of the living organism and develop a series of scattered waves from these discrete volumes;

P. collecting preselected portions of the scattered waves developed in step O with an array of collecting antennas in contact with the surface tissue of the living organism to develop a series of secondary scattered waves from these discrete volumes;

Q. processing each of the secondary scattered waves of step P to separate surface tissue backscatter from the secondary scattered waves and develop a series of segregated scattered waves; and R. shifting a timing of each of the segregated scattered waves such that the segregated scattered returns combine constructively for a preselected volume and detecting an abnormality in the tissue.

14. A non-invasive method of detecting the presence of an abnormality in the tissue of a living organism, according to claim 13, in which step Q includes the sub-step of determining the dielectric characteristics of tissue just below the surface tissue near selected antennas, and including the following additional step:

S. modifying the time shift for each of the segregated scattered waves, step R, according to a propagation time developed from the measured dielectric characteristics of the near-surface tissues.

15. A non-invasive method of detecting the presence of an abnormality in the tissue of a living organism, according to claim 13, including the following additional step:

T. using the scattered returns from a known scattering source to enhance the combined scattered segregated waves from a preselected location.

16. A non-invasive method of detecting the presence of an abnormality in the tissue of a living organism, according to claim 15, in which the preselected location is a portion of the rib cage.

17. A non-invasive method of detecting an abnormality in living tissue, according to claim 13, in which the radiating antenna of step 0 is also used as the collecting antenna of step P.

18. A non-invasive method of detecting an abnormality in living tissue, according to claim 13, in which, in step R, the time shift for the scattered returns is introduced by waveguides that have controllable time delays.

19. A non-invasive method of detecting an abnormality in living tissue, according to claim 13, in which the time shifts for the scattered returns required in Step R are introduced in a digital processing unit employed for Step Q.

20. A non-invasive method of detecting an abnormality in living tissue, according to claim 13, in which the time shifts for the scattered returns required in Step R are introduced by a function that modifies a phase relationships in steps O, P and Q.

21. A non-invasive method of detecting a presence of a tumor or other abnormality in the tissue of a living organism, such as the tissue of a human breast, wherein normal tissue has a predetermined dielectric characteristic different from the dielectric characteristic of a tumor or other abnormality or other tissue, and wherein surface tissue, such as skin, has a different dielectric characteristic than the normal tissue, the method comprising:

V. generating a non-ionizing electromagnetic input wave within a preselected wide band frequency range;

W. applying the input wave of step V to a radiating antenna that is progressively repositioned on surface tissue of a living organism to illuminate minute, discrete volumes at predetermined positions within the tissue of the living organism and develop a series of scattered waves from those volume;

X. collecting a preselected portion of the scattered waves developed by step W by a collecting antenna that is progressively repositioned on the surface tissue of the living organism to develop a series of secondary scattered waves from each collecting position that includes surface tissue scattered waves;

Y. processing each of the secondary scattered waves of step X to separate surface tissue scatter from the secondary scattered waves and develop a series of segregated scattered waves; and Z. shifting a timing of each of the segregated scattered waves such that the scattered returns from a preselected volume combine constructively and detecting an abnormality in the tissue.

22. A non-invasive method of detecting the presence of an abnormality in the tissue of a living organism, according to claim 21, in which step Y includes the sub-step of determining the dielectric characteristics of the tissue just below the surface tissue; and AA. modifying the timing of each of the segregated scattered waves according to a propagation time developed from the measured dielectric characteristics of near surface tissues to enhance the combined returns from a preselected volume.

23. A non-invasive method of detecting the presence of an abnormality in the tissue of a living organism, according to claim 22, and further comprising:

BB. using the scattered returns from a known scattering source to further the timing of each of the segregated waves from each of the preselected locations.

24. A non-invasive method of detecting the presence of an abnormality in the tissue of a living organism, according to claim 23, in which the preselected location is a portion of the rib cage.

25. A non-invasive method of detecting the presence of an abnormality in the tissue of a living organism, according to claim 21, in which the radiating antenna array of step W is the same as the collecting antenna array of step X.

26. A non-invasive method of detecting the presence of an abnormality in the tissue of a living organism, according to claim 21, in which, in step Z, the time shifts for the scattered returns are introduced by waveguides that have controllable time delays.

27. A non-invasive method of detecting the presence of an abnormality in the tissue of a living organism, according to claim 21, in which, in step Z, the time shifts for the scattered returns are introduced in a digital processing unit employed for step Y.

28. A non-invasive method of detecting the presence of an abnormality in the tissue of a living organism, according to claim 21, in which, in step Z, the time shifts for the scattered returns are introduced by a function that modifies phase relationships in steps W, X and Y.

29. A non-invasive method of detecting the presence of an abnormality in the tissue of a living organism, according to claim 21 wherein in step W the radiating antenna remains in a fixed position.

30. A non-invasive method of detecting the presence of an abnormality in the tissue of a living organism, according to claim 21 wherein in step X the collecting antenna remains in a fixed position.

31. A non-invasive method of detecting a presence of a tumor or other abnormality in the tissue of a living organism, such as a tumor on the prostate gland, wherein the normal tissue has a predetermined dielectric characteristic different from the dielectric characteristic of a tumor or other abnormality or other tissue, and wherein surface tissue near the gland, such as the lining of the rectum, has a different dielectric characteristic than the normal tissue, the method comprising:

EE. generating a non-ionizing electromagnetic input wave within a preselected side band frequency range;

FF. applying the input wave of step EE to a radiating antenna positioned on surface tissue of a living organism such that the input wave preferentially illuminates a preselected volume within the tissue of the living organism and develops scattered waves from that volume;

GG. collecting scattered waves from the preselected volume of step FF by a collecting antenna that is positioned on the surface tissue of the living organism to develop a series of secondary scattered waves that include surface tissue scattered waves;

II. processing each of the secondary scattered waves of step GG to separate surface tissue scatter from the secondary scattered waves and develop a series of segregated scattered waves; and KK. combining the segregated scattered waves of step II in a display that shows the position of abnormalities in the tissue.

32. A non-invasive method of detecting an abnormality in the tissue of a living organism, according to claim 31, in which the radiating antenna of step FF is also used as the collecting antenna.

33. A non-invasive method of detecting an abnormality in the tissue of a living organism, according to claim 31, in which the volume of the tissue that is illuminated by the antenna array in step FF is controlled by controlling a time delay of the applied signal to each antenna within the array.

34. A non-invasive method of detecting an abnormality in the living tissue of a living organism, according to claim 31, in which the scattered waves of volume of the tissue that is collected by the antenna array in step GG is controlled by controlling a time delay of the applied signal to each antenna within the array.

35. A non-invasive method of detecting a presence of a tumor or other abnormality in the tissue of a living organism, such as a tumor on the prostate gland, wherein normal tissue has a predetermined dielectric characteristic different from the dielectric characteristic of a tumor or other abnormality or other tissue, and wherein surface tissue near the gland, such as the lining of the rectum, has a different dielectric characteristic than the normal tissue, the method comprising:

LL. generating a non-ionizing electromagnetic input wave within a preselected wide band frequency range;

MM. applying the input wave of step LL to a cylindrical antenna that is positioned on surface tissue of the urethra such that it preferentially is in contact with the skin of a living organism to illuminate a preselected volume within the tissue of the living organism and develops scattered waves from that volume;

NN. collecting scattered waves from the preselected portion of the living tissue by a collecting antenna that is positioned on the surface tissue of the living organism such that it preferentially collects the scattered waves from the preselected volume of step MM to develop a series of secondary scattered waves that includes surface tissue scattered waves;

OO. processing each of the secondary scattered waves of step NN to separate surface tissue scatter and scatter from equipment interfaces from the secondary scattered waves and to develop a segregated scattered wave;

PP. repeating steps MM, NN, and OO to develop another segregated scattered wave from another preselected volume; and QQ. combining the segregated scattered waves of steps NN and PP in a display that shows the position of abnormalities in the tissue.

36. A non-invasive method of detecting an abnormality in the tissue of a living organism, according to claim 35, in which the radiating antenna of step MM is also used as the collecting antenna of step NN.

37. A non-invasive method of detecting an abnormality in the tissue of a living organism, according to claim 35, in which the volume of the tissue that is illuminated by the antenna of step MM is controlled by repositioning the antenna of step MM.

38. A non-invasive system for detecting presence of a tumor or other abnormality in the tissue of a living organism, such as the tissue of a human breast, wherein normal tissue of the organism has a predetermined dielectric characteristic different from the dielectric characteristic of a tumor or other abnormality, and wherein surface tissue such as skin has a different dielectric characteristic than the normal tissue, the system comprising:

a signal generator to generate a non-ionizing electromagnetic input wave within a preselected wide band frequency range;

at least one radiating antenna, connected to the signal generator and aligned with the skin of a living organism, directing at least a portion of the input power into a discrete volume within the tissue of the living organism to illuminate the discrete volume and develop at least one scatter waves reflected from the discrete volume;

at least one collector antenna for collecting at least a portion of the at least one scatter wave from the discrete volume in the living organism;

a signal processor, connected to the at least one collector antennae;

a separator circuit to separate the at least one scatter wave from the preselected volume from the input wave and from other scatter waves from spurious scatter sources; and storage means, connected to the separator, for storing the at least one scatter wave from the preselected discrete volume.

39. A non-invasive system for detecting the presence of a tumor or other abnormality in the tissue of a living organism, according to claim 38, in which the radiating antennae each include two spaced electromagnetically excited conductive surfaces.

40. A non-invasive system for detecting the presence of a tumor or other abnormality in the tissue of a living organism, according to claim 38, in which:

each radiating antenna includes two spaced conductive surfaces which are generally triangular in shape;

the input wave is applied to each conductive surface of each radiating antenna in phase opposition; and the system further comprises a balun to convert an unbalanced input wave to a balanced, oppositely phased input wave.

41. A non-invasive system for detecting the presence of a tumor or other abnormality in the tissue of a living organism, according to claim 40, in which the electrical parameters of materials used for each radiating antenna are spatially distributed to suppress unwanted reflections.

42. A non-invasive system for detecting the presence of a tumor or other abnormality in the tissue of a living organism, according to claim 38, in which the radiating antennae are encapsulated in a radiating antenna array, the encapsulating material of the radiating antennae having a dielectric characteristic between the dielectric characteristics of normal breast tissue and surface tissue.

43. A non-invasive system for detecting the presence of a tumor or other abnormality in the tissue of a living organism, according to claim 42, in which the relative dielectric constant of the encapsulating material is in a range of 4 to 40.

44. A non-invasive system for detecting the presence of a tumor or other abnormality in the tissue of a living organism, according to claim 42, and further comprising:

positioning means for positioning the radiating antennae at a given known location in direct contact with the skin of a human breast.

45. A non-invasive system for detecting the presence of a tumor or other abnormality in the tissue of a living organism, according to claim 44, in which the positioning means includes encapsulating material, similar to the material which encapsulates the radiating antennae, having a dielectric characteristic that is between the dielectric characteristics of normal breast tissue and of the skin tissue.

46. A non-invasive system for detecting the presence of a tumor or other abnormality in the tissue of a living organism, according to claim 45, in which the relative dielectric constant of the encapsulating material is in a range of 4 to 40.

47. A non-invasive system for detecting the presence of a tumor or other abnormality in the tissue of a living organism, according to claim 38, in which the system further comprises time averaging means for averaging the amplitude of collected scatter waves over a predetermined time period to enhance the signal-to-noise ratio of the collected scatter waves.

48. A non-invasive system for detecting the presence of a tumor or other abnormality in the tissue of a living organism, according to claim 38, in which at least one radiating antenna forms a tubular beam to illuminate the discrete volume.

49. A non-invasive system for detecting the presence of a tumor or other abnormality in the tissue of a living organism, according to claim 48, in which:

at least one radiating antenna and at least one collector antenna are the same.

50. A non-invasive system for detecting the presence of a tumor or other abnormality in the tissue of a living organism, according to claim 38, in which the system further comprises:

at least one switching circuit, interposed between the signal generator and the radiating antennae, to modify the input wave so that it is directed into a second discrete volume within the tissue of the living organism.

51. A non-invasive system for detecting the presence of a tumor or other abnormality in the tissue of a living organism, according to claim 50, in which the system further comprises:

at least one switch interposed between each collector antenna and the signal processor.

* * * * *